(12) United States Patent
Yoo et al.

(10) Patent No.: US 7,053,262 B2
(45) Date of Patent: May 30, 2006

(54) MAMMARY GLAND TISSUE-SPECIFIC EXPRESSION SYSTEM USING β-CASEIN PROMOTER SITE OF KOREAN NATIVE GOAT

(75) Inventors: Ook Joon Yoo, Kyunggi-do (KR); Kyung Kwang Lee, Taejeon (KR); Young Mahn Han, Taejeon (KR); Sun Jung Kim, Taejeon (KR); Hae Young Jeong, Taejeon (KR); Jung Ho Ko, Taejeon (KR); Won Jun Oh, Seoul (KR)

(73) Assignee: Hanmi Pharm Co., Ltd. (KR)

( * ) Notice: Subject to any disclaimer, the term of this patent is extended or adjusted under 35 U.S.C. 154(b) by 400 days.

(21) Appl. No.: 10/347,718

(22) Filed: Jan. 17, 2003

(65) Prior Publication Data

US 2003/0145342 A1  Jul. 31, 2003

Related U.S. Application Data

(62) Division of application No. 09/582,490, filed as application No. PCT/KR98/00277 on Sep. 11, 1998, now Pat. No. 6,635,474.

(51) Int. Cl.
*C12P 21/00* (2006.01)
*C12N 15/63* (2006.01)

(52) U.S. Cl. ............... 800/4; 435/320.1; 435/325
(58) Field of Classification Search ............ 800/3; 435/320.1

See application file for complete search history.

(56) References Cited

FOREIGN PATENT DOCUMENTS

| JP | 9-37786 | 2/1997 |
|---|---|---|
| WO | WO 95/17085 | 6/1995 |

OTHER PUBLICATIONS

Sigmund, C.D. 2000. Arterioscler Thromb Vasc Biol. 20:1425-1429.*
Wall, R.J. 1996. Theriogenology 45:57-68.*

* cited by examiner

*Primary Examiner*—Celine Qian
(74) *Attorney, Agent, or Firm*—Knobbe, Martens, Olson & Bear, L.L.P.

(57) ABSTRACT

The mammary gland-specific expression systems developed by the present inventors, named pGbc, pGbc_L and pGbc_S were deposited under the Budapest Treaty on the International Recognition of the Deposit of Microorganisms for the Purpose of Patent Procedure in the Korean Collection for Type Cultures (KCTC), Korean Research Institute of Bioscience and Biotechnology at 52, Oun-dong, Yusong-Ku, Taejon 305–333, Republic of Korea, on Aug. 17, 1998, and the accession deposit Nos. KCTC 0515BP, 0514BP and 0513BP were issued, respectively. All restrictions on the availability to the public of the deposited materials will be irrevocably removed upon the granting of a patent. The systems of the present invention make it possible that desired proteins are produced by expression in mammary gland tissue-derived animal cells or through the milk secreted from the transgenic animals with the expression systems, thereby solving the above-mentioned problems, that is, the activity sustenance, production cost, and isolation and purification of the desired proteins.

2 Claims, 16 Drawing Sheets

Fig.2

```
   1 aagcttcttt ctttagtata ttgttaagga tttcttgatc aagattttac ctacttttct
  61 ggtccaattg gtgagagaca gtcataagga aatgctgtgt ttattgcaca atatgtaaag
 121 catcttcctg agaaaataaa agggaaatgt tgaatgggaa ggatatgctt tcttttgtat
 181 tcctttctg agaaatcaga cttttcacc tgtggccttg gcacaaaagc taacaaataa
 241 aggcatatga agtagccaag gcctttcta gtatatctat gacactgagt tcatttcatc
 301 atttattttc ctgacttcct cctgggtcca tatgagcagt cttagaatga atattagctg
 361 ataatccaa atacatagta gatgttgatt tgggttttct aagcaatcca agacttgtat
 421 gacagtaaga tgtattacca tccaacaaca cacatctcag catgatataa atgcaaggta
 481 tattgtgaag aaaaatttt aattatgtca aagtgcttac tttagaaggt catctatctg
 541 tcccaaagct gtgaatatat atattgaagg taatgaatag atgaagctaa ccttgtaaaa
 601 atgagtagtg tgaatacaac tacaattatg aacatctgtc actaaagagg caaagaaact
 661 tgaagattgc ttttgcaaat gggctcctat taataaaaag tactttgag gtctggctca
 721 gactctattg tagtacttag ggtaataccc tcctcctgta tgggctttca ttttctttct
 781 tgcttccctc atttgcccct tccatgaatga ctagctgata aagcattgac tataaaagat
 841 atgaggccaa acttgagctg tcccattta ataaatctgt ataataatat tgttctacaa
 901 aagtattatc taaataaatg ttactttctg tcttaaaatc cctcaacaaa tccccactat
 961 ctagaggatc cgattgacat tccctggaat cacagcatgc tttgtctgcc attatctgac
1021 ccctttctct ttctctcttc tcacctccat ctactccttt ttccttgcaa ttcatgaccc
1081 agattcactg tttgatttgg cttgcatgtg tgtgtgctga gttgcgtctg actgttatca
1141 accccatgaa tgatagtcca ccaggctcta ctgtccatga aatttccag tcaagaatac
1201 tggagtggat tgcatttcct actccatttg attaatttag tgactttaa atttctttt
1261 ccatattcgg gagcctattc ttccttttta gtctatactc tcttcactct tcaggtctaa
1321 ggtatcatcg tgtgcttgtt agcttgttac tttctccatt atagcttaag cactaacaac
1381 tgttcaggtt ggcatgaaat tgtgttcttt gtgtggcctg tatatttctg ttgtgtatta
1441 gaatttaccc caagatctca aagacccact gaatactaaa gagacctcat tgtggttaca
1501 ataatttggg gactgggcca aaacttccgt gcatcccagc caagatctgt agctactgga
1561 caattcatt tcctttatca gattgtgagt tattcctgtt aaaatgctcc ccagaatttc
1621 tggggacaga aaaataggaa gaattcattt cctaatcatg cagatttcta ggaattcaaa
1681 tccactgttg gttttatttc aaaccacaaa attagcatgc cattaaatac tatatataaa
1741 cagccactaa atcagatcat tatccattca gcttctcctt cacttcttct cctctacttt
1801 ggaaaaaagg taagaatctc agatataatt tcagtgtatc tgctactcat ctttattttg
1861 gactaggtta aaatgtagaa agaacataat tgcttaaaat agatcttaaa aataagggtg
1921 tttaagataa ggtttacact attttcagca gatatgttaa aaaatagaag tgactataaa
1981 gacttgataa aaattatagg tgactgcaa
```

C : commercial hGM-CSF
S : pGbc_S-hGMCSF transfected
L : pGbc_L-hGMCSF transfected
H : HC11 cell, not transfected

MAMMARY GLAND TISSUE-SPECIFIC EXPRESSION SYSTEM USING β-CASEIN PROMOTER SITE OF KOREAN NATIVE GOAT

RELATED APPLICATIONS

This application is a divisional of U.S. application Ser. No. 09/582,490, filed Nov. 14, 2000, now U.S. Pat. No. 6,635,474 which is the U.S. National Phase of International Application PCT/KR98/00277, filed Sep. 11, 1998 and published in English on Mar. 23, 2000 as WO 00/15808.

TECHNICAL FIELD

The present invention relates to a mammary gland tissue-specific expression system using the promotor site for the β-casein gene of Korean native goats, through which physiological activating substances can be produced. More particularly, the present invention relates to novel recombinant mammalian expression vectors in which a β-casein gene expression-regulating region, a physiological activating substance gene and a termination-regulating region are linked. Also, the present invention is concerned with a method for producing physiological activating substances in mammary gland tissue-derived cell lines and in animals, using the novel recombinant vectors.

BACKGROUND ART

Physiological activating substances are produced and secreted at trace amounts in the human body and play an essential role in various metabolisms and modulations. The physiological activating substances known to date include insulin, interleukins, hemopoietic growth regulating factors, such as stem cell factor, granulocyte colony stimulating factor, erythropoietin, etc, and are too numerous to describe their great functions in the human body, in detail. The reason why such physiological activating substances, in spite of their importance, have not yet been industrialized, is that they are difficult to isolate and purify owing to their trace amount in the human body. Further, the physiological activating substances produced by using a procaryotic expression system, such as that obtained from E. coli, frequently do not perform their normal functions in the human body as well as have not yet overcome the safety problem which must be solved before administration.

According to the reports contributed to the academic circles, it is known that, even if there is used a promotor site for a gene which is expressed specifically in a mammary gland tissue, the expression level is different depending on the species from which the promotor is obtained and on the genes to be expressed (Clark et al. (1987) Trends Biotech. 5, 20–24; Simons et al., (1987) Nature 328, 530–532; Lee at al., (1988) Nucl. Acids Res. 16, 1027–1041; Vilotte et al., (1988) Eur. J. Biochem. 186, 43–48; Gorden et al., (1987) Bio/Technology 8, 443–446; Shani et al., (1992) Transgenic Res. 1, 195–208; Wright et al., (1991) Bio/Technology 9, 830–834; Ebert et al., (1991) Bio/Technology 9, 835–838; Mega et al., (1994) Transgenic Res. 3, 36–42; Wei et al., (1995) Transgenic Res. 4, 232–240; Gutierrez et al., (1996) Transgenic Res. 5 271–279)

In order to produce physiological activating substances, the expression systems which take advantage of E. coli (Korean Pat. Publication No. 94-5585) and animal cells have been usually used. These techniques would occasionally bring about industrial successes, but still have significant problems to be solved. For instance, in the case of the expression utilizing E. coli, mass production is possible with low cost. However, since E. coli, a prokaryote, does not perform a posttranslational modification, which is a feature of eukaryotes, such a human physiological activating substance as EPO cannot exert its activity if it is produced in E. coli. To avoid this problem, active research has been and continues to be directed to the development expression systems which take advantage of animal cells. The products expressed in these systems are active in the human body because they experience posttranslational modifications. However, the problem of high cost for culturing animal cells remains unsolved.

Almost all of the physiological activating substances that are industrially produced utilize the above mentioned techniques, so they have the problems to be solved, including activity sustenance, cost, and isolation and purification.

DISCLOSURE OF THE INVENTION

One aspect of the present invention provides a method for producing physiological activating substances. The method comprises expressing said physiological activating substances using one or more vectors selected from the group consisting of pGbc, pGbc_L, and pGbc_S. The method can be performed either in vitro or in vivo. The physiological activating substances are expressed in mammary gland tissue-derived cells. The physiological activating substances are expressed in transgenic animals. The mammary gland tissue-derived cells comprises HC11. The HC11 cells are transfected by calcium phosphate coprecipitation or electroporation. The transgenic animals are made by microinjection into the male pronucleus of the animals.

The mammary gland-specific expression systems developed by the present inventors, named pGbc, pGbc_L and pGbc_S, deposited in the Korean Collection for Type Cultures, Korean Research Institute of Bioscience and Biotechnology, on Aug. 17, 1998 (deposition Nos. KCTC 0515BP, 0514BP and 0513BP, respectively) make it possible that desired proteins are produced by expression in mammary gland tissue-derived animal cells or through the milk secreted from the transgenic animals with the expression systems, thereby solving the above-mentioned problems, that is, the activity sustenance, production cost, and isolation and purification of the desired proteins.

Use of the expression-regulating region of a β-casein gene, expressed specifically in mammary gland tissues, in producing human physiological activating substances, brings about the following industrial advantages. First, because the target proteins which are produced by the recombination technique of the present invention experience the same posttranslational modification as that which the corresponding naturally occurring proteins do, the target proteins can sustain their activity in the human body. Secondly, by virtue of taking advantage of specificity for mammary gland tissue, the expression systems of the present invention employing mammary gland tissue-derived cells or transgenic animals can produce physiological activating substances at much lower cost than do the expression systems using general animal cells. The proteins produced in mammary gland tissue-derived cells or through the milk secreted from transgenic animals are few in number, so that the target protein is easy to isolate and purify. Additionally, transgenic animals require no further significant cost in scaling-up the production of the target proteins as well as produce no pollution during its production. A third advantage is the safety of the physiological activating substances produced. Because there are no toxins in the products secreted from the mammary gland tissues, the expression system of the present invention is safer than other conventional systems.

In order to producing physiological activating substances, methods utilizing *E. coli*, or animal cells were developed and more recently, advantage has been taken of transgenic animals. The expression techniques using *E. coli* as a host or using animal cells have now a limitation in industrial application owing to the above-mentioned problems, that is, the activity sustenance, production cost, and isolation and purification of the physiological activating substances produced. As a measure of settling these problems, transgenic animal and related techniques have rapidly developed and now make a great advance in biological studies.

The present invention uses a mammary gland tissue-derived cell line and a transgenic animal in producing proteins. For this, molecular biological technology and other apical techniques are employed in the present invention. For example, DNA recombination techniques are needed for constructing the mammalian expression vectors which are able to be expressed specifically in mammary gland tissues and a microinjection technique is for producing a transgenic animal with the vectors.

Although it is well known to those skilled in the art to use the promoter sites of the genes expressed specifically in mammary gland tissues in constructing a mammalian expression vector which is able to express proteins specifically in the mammary gland tissues and the mammalian expression vector of the present invention is originated from pRC/RSV, a commercial vector (Invitrogen Inc.), the expression systems of the present invention is quite different from those of other conventional techniques in the following aspects. First, the goat β-casein promoter used in the present invention is obtained from Korean native goats. A second characteristically different point is that the goat β-casein promoter site is linked to the first exon of a structural gene via the first exon of the goat β-casein gene. In most cases, an intron is interposed between a promotor site and the first exon of a structural gene. Third, in the mammalian expression vectors according to the present invention, a bovine growth hormone follows a structural gene, with the aim of accomplishing a preferable transcription termination. Irrespective of whether the poly A signal of the structural gene is present or not, the bovine growth hormone terminator is linked to the structural gene.

BRIEF DESCRIPTION OF THE DRAWINGS

The above and other objects and aspects of the invention will become apparent from the following description of embodiments with reference to the accompanying drawings in which:

FIG. 2. is the base sequence of the β-casein promoter of Korean native goats (SEQ ID NO:1);

BEST MODES FOR CARRYING OUT THE INVENTION

[1] Construction of Expression Vectors

Figure 1:
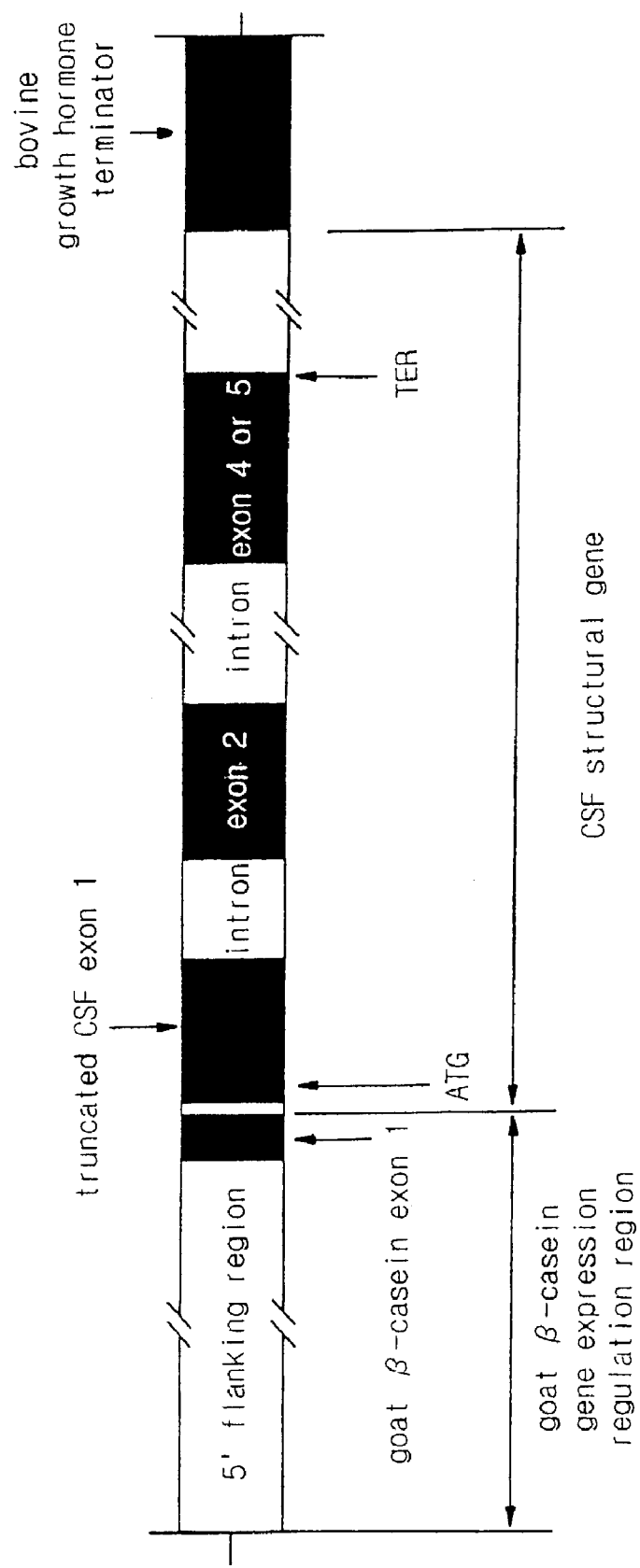
FIG. 1 a schematic view showing a portion of the common structure of novel vectors pGbc_S and pGbc_L for transfection into animal cells and a novel vector pGbc for transgenic animals.

1) Amplification of the B-casein Promotor and Exons 1 and 2 of Korean Native Goats Two pairs of primers are designed to amplify through a polymerase chain reaction (PCR) a portion of the β-casein gene which was reported to be expressed specifically in Korean native goats. One pair of the primers is responsible for the amplification of a partial gene including the goat β-casein promoter site and exon 1 and the other for the amplification of a partial gene including the goat β-casein intron 1 and exon 2. The PCR product for the goat β-casein promoter and exon 1 is digested with endonucleases Sac I and Hind III while the PCR product for the goat β-casein intron 1 and exon 2 with endonucleases Hind III and Sal I. The two upstream and downstream primers for the amplification of the goat β-casein and exon 1 are named GBC-F1 (SEQ ID NO:2) and GBC-R1 (SEQ ID NO:3), respectively and have the following base sequences: GBC-F1, 5'-GCT GAG CTC TTT AGT ATA TTG TTA AGG A-3'; and GBC-R1, 5'-TGT CAA GCT TAT CTT AAA CAC CCT TA-3'. The two upstream and downstream primers for the amplification of the goat β casein intron 1 and exon 2 are named GBC-F2 (SEQ ID NO:4) and GBC-R2 (SEQ ID NO:5), respectively, and have the following base sequences: GBC-F2, 5'-GCA TAA GCT TTA CAC TAT TTT CAG CAG-3'; and GBC-R2, 5'-ATA GTC GAC CCA GAG TTG TGG TC-3'. After the two digested PCR products together are inserted in a pBluescript II SK vector, commercially available from Stratagene, the resulting plasmid is subjected to double strand sequencing analysis to identify the base sequence of the ligated gene fragments.

2) Construction of PGbc_S and pGbc_L

Of the gene region subcloned in the pBluescript II SK (Stratagene), a stretch of DNA ranging from 501 nucleotides to one nucleotide on the upstream side of the translation start codon for exon 1 is amplified by PCR. This PCR product is digested with restriction enzymes Nru I and Hind III. Separately, pRC/RSV, a mammalian expression vector, is treated with the same enzymes to remove the LTR region. To this opened plasmid, the digested PCR product is inserted by ligation to give pGbc_S.

The digested PCR product is further treated with restriction enzyyme Dra I and extraction and purification are made for the gene fragment whose opposite ends are cut by Hind III and Dra I. The pBluescript II SK comprising the goat β-casein promoter, exon 1, intron 1 and exon 2 regions is subjected to double digestion with restriction enzymes Stu I and Dra I, followed by extraction and purification for the fragment comprising no exon 1 gene. These two gene fragments together are ligated to a pRc/RSV vector which is previously cleaved by Nru I and Hind III, to give pGbc_L.

Whether pGbc_S and pGbc_L are correctly constructed or not is confirmed by base sequencing analysis.

3) Construction of pGbc and Recombination with Physiological activating substance Genes (human Granulocyte Colony Stimulating Factor (hGCSF) and human Granulocyte Macrophage Colony Stimulating Factor (hGMCSF))

The PCR product A gene fragment including the promoter site and exon 1 region is double-digested with Sac I and Dra I to give a gene fragment including the promoter site and a partial exon 1 extending to one nucleotide on the 5' side of the translation start codon. Separately, the PCR product 500 bp in size obtained in 2) above, is digested with Dra I and Hind III. By ligation, these two gene fragments are together inserted in a Sac I/Hind III-cleaved pBluescript II SK vector (Stratagene) which is, then, opened by the cleavage with Hind III and EcoR I. To this opened plasmid, a truncated gene fragment which includes a structural gene linked to a bovine growth hormone terminator and which is truncated with Hind III and EcoR I, is ligated. The general structure of the pGbc type vectors is schematically shown in FIG. 1.

[2] Recombination of Mammary Gland Tissue-Specific Expression Vectors & hGCSF Gene and hGMCSF Gene 1) Using well-known gene search and PCR techniques (Sambrook et al. (1989) Molecular Cloning: A Laboratory Manual, Cold Spring Harbor Press, New York), an hGCGF gene and an hGMCSF gene are cloned in pUC19, a plasmid vector commercially available.

2) Recombination of hGCSF Gene and Mammary Gland Tissue-Specific Expression Vectors pGbc_S and pGbc_L The pUC19 vector in which the hGCSF gene is cloned is digested with restriction enzymes BamH I and Xba I. Fragment 1, which includes a region ranging from exon 2 through a poly A signal, is isolated and purified. The vector thus opened is digested with restriction enzyme Pst I to give Fragment 2 which includes a region ranging from one nucleotide on the 5' side of the translation start codon through one nucleotide on the 5' side of the exon 2. Fragments 1 and 2 are inserted and ligated to a pBluescript II SK vector which is opened with restriction enzymes Pst I and Xba I, to produce a recombinant plasmid pBluescript II SK-hGCSF. This plasmid is subjected to double digestion with endonucleases Hind III and Xba I to obtain a modified hGCSF gene which is, then, ligated to a pGbc_S vector which is digested at the same endonuclease sites Hind III and Xba I, to make a novel plasmid pGbc_S-hGCSF.

Similarly, a novel plasmid pGbc_L-hGCSF is constructed by ligating a fragment which is obtained by the endonuclease digestion of a goat β-casein promoter and a modified hGCSF gene fragment which is obtained by double digestion of the pBluescript II SK-hGCSF with Hind III and Xba I to a pGbc_L vector opened with the same endonucleases.

3) Recombination of hGMCSF Gene and Mammary Gland-Specific Expression Vectors pGbc_S and pGbc_L The hGMCSF gene which is subcloned in the pUC19 vector is extracted by digestion with restriction enzymes BamH I and EcoR I and then, inserted by ligation to a pBluescript II SK vector (Stratagene) which is digested with the same endonucleases, to produce a recombinant plasmid pBluescript II SK-hGMCSF. A modified gene is recovered by the digestion of the recombinant plasmid with Hind III and Xba I and then, ligated to a pGbc_S vector which is digested at the same endonuclease sites Hind III and Xba I, to construct a novel plasmid pGbc_S-hGMCSF.

Similarly, a novel plasmid pGbc_L-hGMCSF is constructed by ligating a fragment which is obtained by the endonuclease digestion of a goat β-casein promoter and a modified hGMCSF gene fragment which is obtained by double digestion of the pBluescript II SK-hGMCSF with Hind III and Xba I to a pGbc_L vector opened with the same endonucleases.

The successful construction of the expression vectors is confirmed through base sequencing analysis.

[3] Transfection of pGbc_S-hGCSF/hGMCSF and pGbc_L-hGCSF/hGMCSF into Mouse Mammary Gland Tissue-derived HC11 cell and Expression Induction with Lactating Hormone 1) Culture of HC11 Cell Strain HC11 cells are cultured in RPMI media, commercially available from Gibco BRL, supplemented with fetal bovine serum at a final concentration of 10%, epidermal growth factor at 10 ng/ml, insulin at 5 μg/ml and gentamicin (Sigma) at 50 μg/ml.

2) Transfection of pGbc_S-hGCSF, pGbc_S-hGMCSF, pGbc_L-hGCSF and pGbc_L-hGMCSF into HC11 Cells The four novel plasmids constructed in the present invention are purified by using QIAGEN-tip 100, commercially available from Qiagen company, according to the protocol recommnended by Qiagen company. The introduction of the purified plasmids into HC11 cells is performed using an electroporator, manufactured by Invitrogen. A detailed procedure follows the protocol recommended by the provider.

3) Selection with Antibiotics

The HC11 cells are transferred to T25 flasks and cultured for 24–48 hours in an incubator which is maintained at 5% $CO_2$ and at 37° C., after which the culture media are changed with fresh RPMI 1640 media (Gibco BRL), supplemented with fetal bovine serum at a final concentration of 10%, epithermal growth factor at 10 ng/ml, insulin at 5 μg/ml, and antibiotics gentamicin (Sigma) at 50 μg/ml and geneticin (Sigma) at 200 μg/ml, to select the transfected cells.

4) Expression Induction with Lactating Hormone

After the selection, the selective media are changed with induction media comprising RPMI 1640 media (Gibco BRL) supplemented with insulin at a final concentration of 5 µg/ml, geneticin (Sigma) at 200 µg/ml, gentamicin 50 µg/ml, goat prolacitin at 5 µg/ml and dexamethasone at 1 µm. The cells are cultured in a 5% $CO_2$, 37° C. incubator for 4 days without refreshing the media.

5) Expression Level Assay

The human physiological activating substances produced as a result of the expression induction of their genes are secreted into the media. A Western blotting technique is used for the qualitative analysis of the secreted products while an enzyme linked immunosorbent assay (ELISA) is for a quantitative analysis. As a primary antibody for the Western blotting, anti-human G-CSF mouse Ig G monoclonal or polyclonal antibody is used for the analysis of the expression of human granulocyte colony stimulating factor and anti-human GM-CSF mouse Ig G for the analysis of the expression of human granulocyte macrophage colony stimulating factor. Horse radish peroxidase-conjugated anti-mouse Ig G is used as a secondary antibody for the Western blotting. For ELISA, anti-human G-CSF goat Ig G polyclonal antibodies or anti-human GM-CSF goat Ig G polyclonal antibodies are first attached on 96 well plates which are, then, treated with the expressed product as a corresponding antigen or with a commercially available factor used as a standard. To these were linked the anti-human G-CSF or anti-human GM-CSF monoclonal antibody which is the same as used in the Western blotting. The resulting antibody complexes are treated with alkali phosphatase-conjugated anti-mouse Ig G monoclonal antibody with the aim of inducing a coloring reaction (Ed Harlow and Davis Lane (1989) *Antibodies A Laboratory Manual*, Cold Spring harbor Laboratory Press, New York).

[4] Expression in Transgenic Mouse

1) Purification of the Vectors for Transfection

For purifying the vectors for transfection from *E. coli*, QIAGEN tip 100 (Qiagen) and Elutip (Schleicher & Schuell) are used. First, the vectors for transfection are purified with the aid of QIAGEN tip 100. The purified vectors are digested with restriction enzymes, followed by extraction with a Geneclean II kit. The extracted vectors are further purified by following the protocol recommended by Schleicher & Schuell and then, dialyzed in a solution comprising 10 mM Tris•Cl (pH 7.2) and 10 mM EDTA, to produce a vector at an amount of 40 ng/ml, which is later used for microinjection.

2) Microinjection

Into the male pronuclear site of a CBA line mouse oosperm, the finally purified expression vector is introduced by microinjection. This oosperm is nidated in the womb of a surrogate mother by using a surgical operation technique.

3) Genomic DNA Isolation and Gene Induction Assay

The progenies from the surrogate mother have their tails cut. From them, genomic DNA is isolated and purified according to a known method (Vilotte, J. -L. et al., (1989) *Eur. J. Biochem.* 186, 43–48). Whether the desired gene is correctly introduced into the mice or not is identified by appropriate methods including Southern blotting and PCR.

4) Milk Extraction and Expression Level Assay

The progeny mice into which the genes are introduced correctly are let to copulate non-transgenic, normal mice to produce next generation progenies. 10 days after birth, the transgenic parturient mice are segregated from the their offspring for 3 hours. Following peritoneal injection of oxytocin, milk is extracted from the parturient mice. The expression level of the genes is assayed in the same manner as in cell level, using Western blotting and ELISA for qualitative and quantitative analyses, respectively.

Now, a further description will be given of the expression system according to the present invention, with reference to the drawings.

Referring to FIG. 1, there is a gene structure showing recombinant vectors pGbc_S, pGbc_L and pGbc. The first two vectors are constructed for the expression in animal cells while the last is for transgenic mouse. As shown in FIG. 1, this gene structure comprises a goat β-casein gene expression regulation region, a CSF structural gene region and a bovine growth hormone terminator region.

The β-casein gene expression regulation region consists of a partial β-casein exon 1 which extends only to one nucleotide on the 5' side of the translation start codon, and a 5' flanking region including goat β-casein promoter site.

In the CSF structural gene region, "ATG", the start codon, is written to emphasize that it comes from the physiological activating substance to be expressed, itself. The hG-CSF gene consists of 4 exons whereas the hGM-CSF gene of 5 exons, for which "exon 4 or 5" stands. "TER" denotes the termination codon for the CSF gene.

In this figure, the distances of the regions are not proportional to their actual lengths.

FIG. 2 is the base sequence of the β-casein promoter from the Korean native goat utilized in the present invention (SEQ ID NO:1). The base sequence is identical to that of *Capra hircus* β-casin promoter and exon 1, reported by Roberts, B. T., Ditullio, P., Vitale, J., Hehir, K., and Cordon, K. in *Gene* (1992) 121, 255–262.

Figure 3:
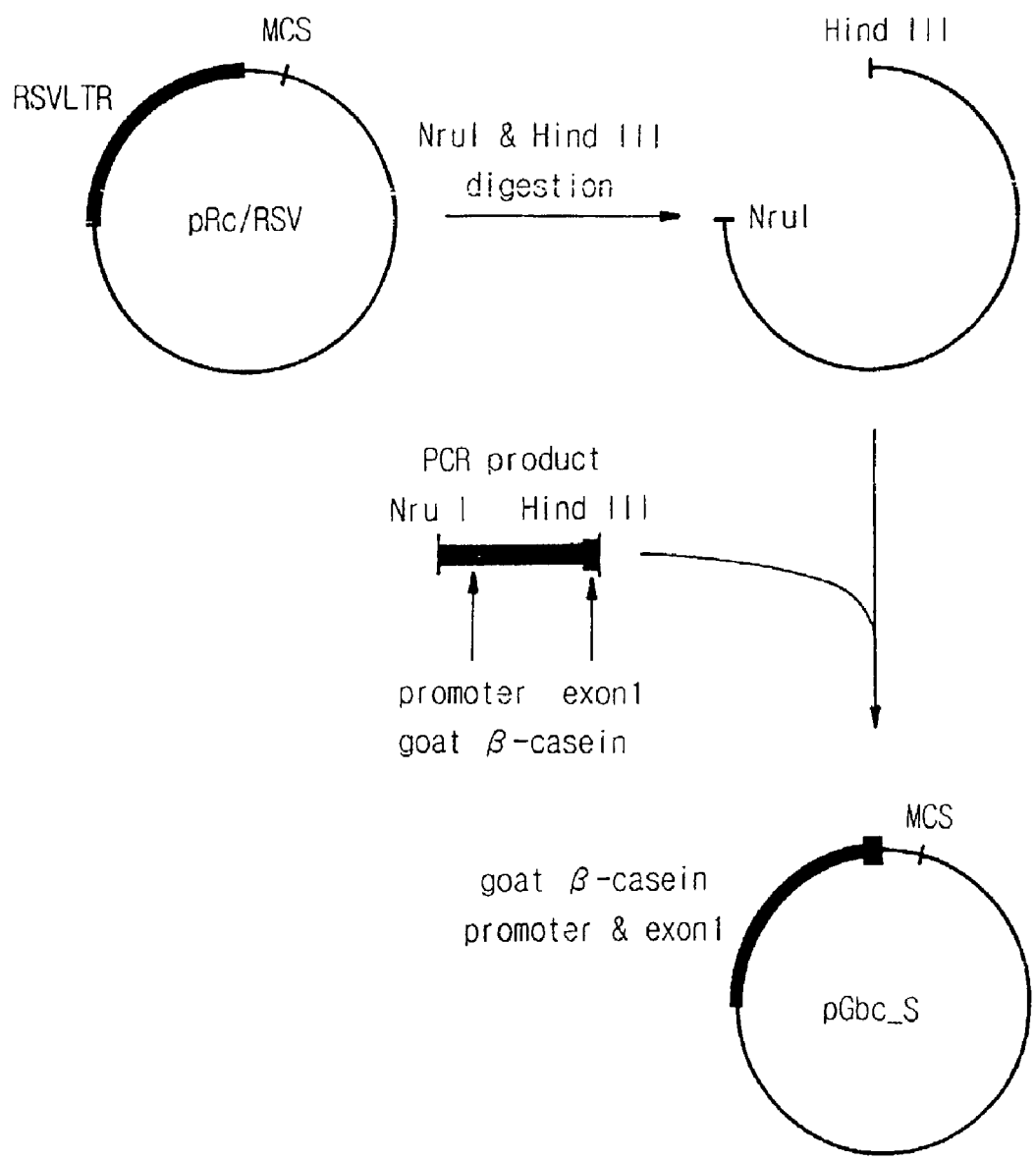
FIG. 3 is a schematic diagram illustrating the construction of the recombinant vector pGbc_S, according to the present invention.

With reference to FIG. 3, there is schematically shown a construction procedure for the recombinant vector pGbc_S. In the figure, the length of each region does not reflect the scale of its actual length. That two lines join together into one arrow line illustrates ligation while MCS stands for the multicloning site, PCR product is the product obtained by a polymerase chain reaction, and RSV LTR represents Rous sarcoma virus long tandem repeat. The thicker lines in the PCR product and pGbc_S illustrations denote the exon 1 of a goat β-casein gene. Restriction enzymes are positioned over their own recognition sites on the illustrations.

Figure 4:
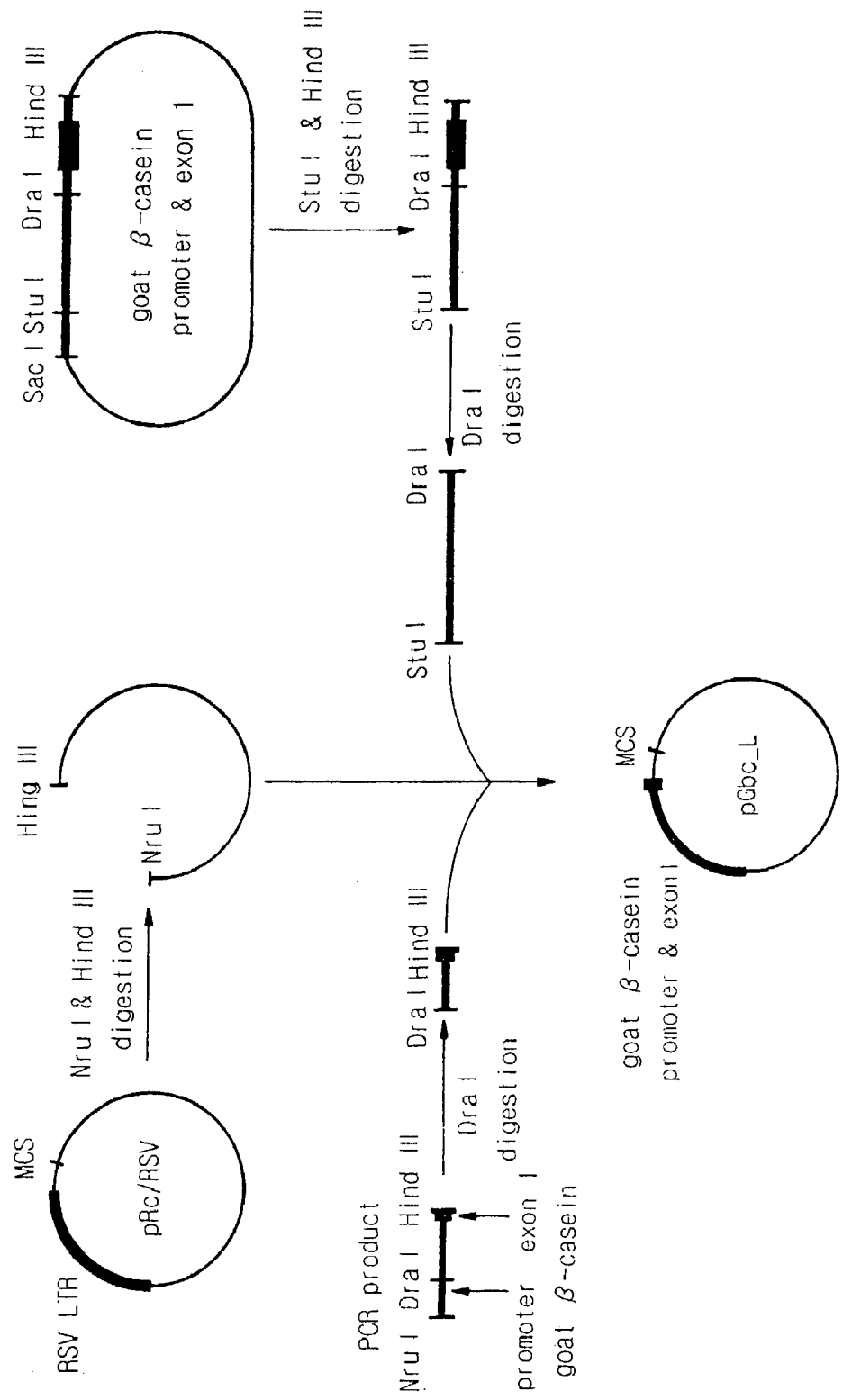
FIG. 4 is a schematic diagram illustrating the construction of the recombinant vector pGbc_L, according to the present invention.

With reference to FIG. 4, there is schematically shown a construction procedure for the recombinant vector pGbc_L. In the figure, the length of each region does not reflect the scale of its actual length. One arrow line into which three lines join together stands for ligation, MCS stands for the multicloning site, PCR product is the product obtained by a polymerase chain reaction, and RSV LTR is Rous sarcoma virus long tandem repeat. The thicker lines in the PCR product, goat β-casein promoter & exon 1 and pGbc_L illustrations denote the exon 1 of a goat β-casein gene.

Figure 5:
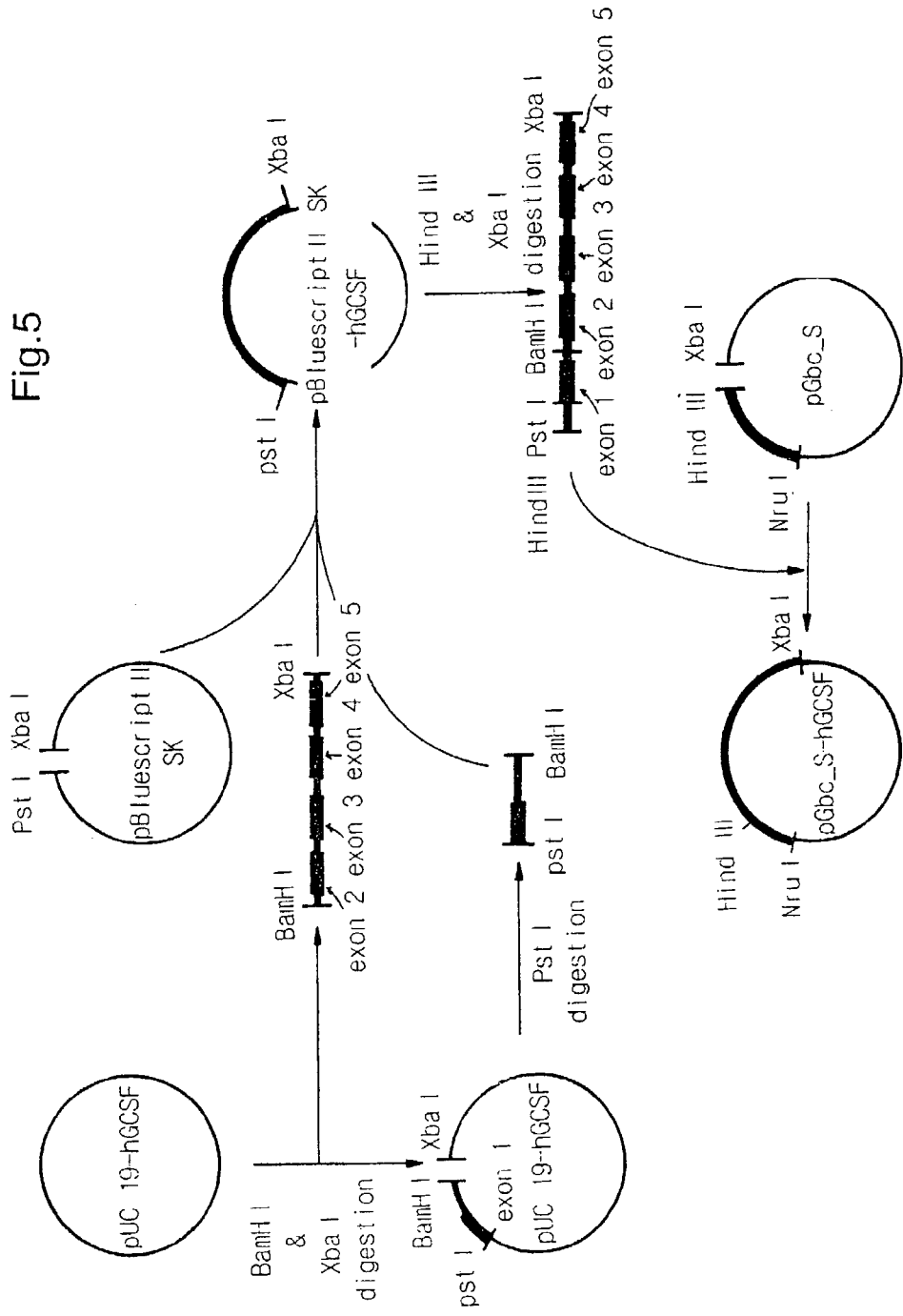
FIG. 5 is a schematic diagram illustrating the recombination of the vector pGbc_S with a hGCSF gene, according to the present invention.

With reference to FIG. 5, there is schematically shown a procedure for the recombination between the plasmid pGbc_S and the hGCSF gene.

In this figure, the lengths of plasmids and DNA fragments are only illustrative, but do not reflect the scale of their actual lengths. Restriction enzymes are positioned over their own recognition sites on the illustrations. Ligation is expressed by joining two or more lines together into one arrow line. Exon genes are expressed by thicker lines than those expressing intron genes. In pBluescript II SK-hGCSF, pGbc_S and pGbc_S-hGCSF illustrations, exons and introns are indiscriminately expressed.

Figure 6:
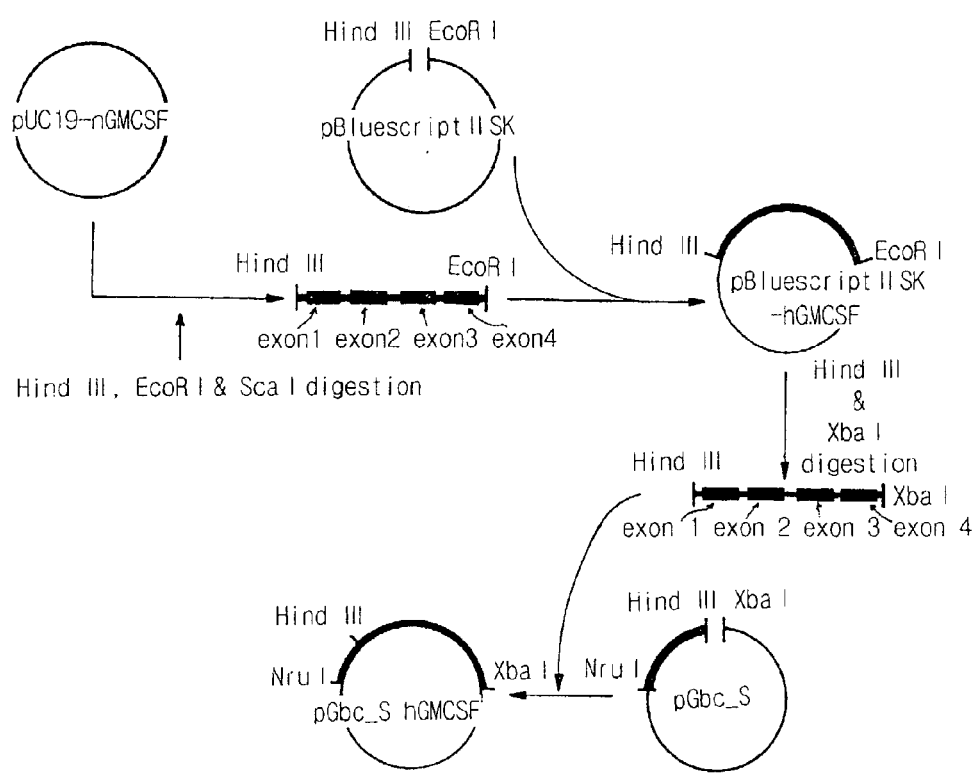
FIG. 6 is a schematic diagram illustrating the recombination of the vector pGbc_S with a hGMCSF gene, according to the present invention.

With reference to FIG. 6, there is schematically shown a procedure for the recombination between the plasmid pGbc_S and the hGMCSF gene.

In this figure, the lengths of plasmids and DNA fragments are only illustrative but do not reflect the scale of their actual lengths. Restriction enzymes are positioned over their own recognition sites on the illustrations. Ligation is expressed by joining two or more lines together into one arrow line. Exon genes are expressed by thicker lines than those expressing intron genes. In pBluescript II SK-hGMCSF, pGbc_S and pGbc_S-hGMCSF illustrations, exons and introns are indiscriminately expressed.

Figure 7:
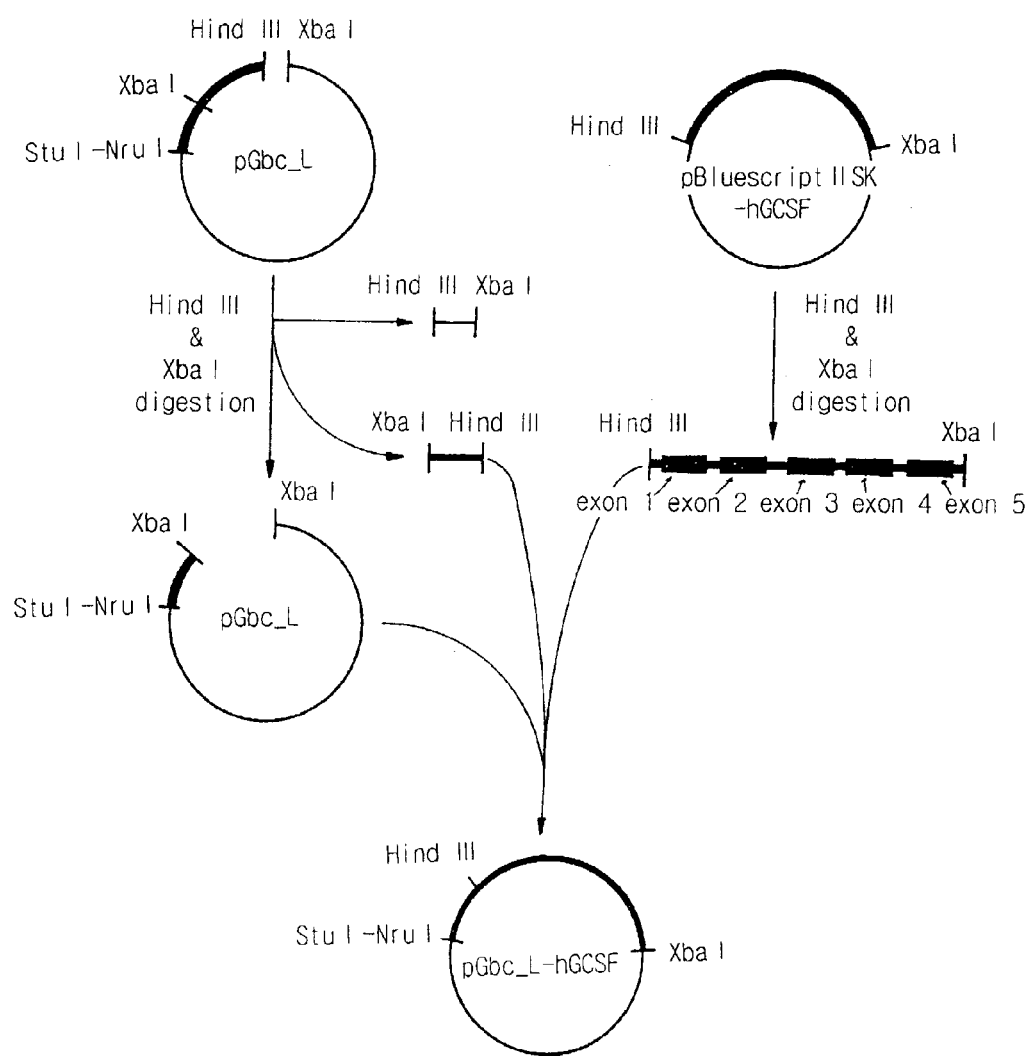
FIG. 7 is a schematic diagram illustrating the recombination of the vector pGbc_L with a hGCSF gene, according to the present invention.

FIG. 7 is a schematic diagram showing a procedure for the recombination between the plasmid pGbc_L and the hGCSF gene.

In this figure, the length of each of the plasmids and DNA fragments does not reflect the scale of its actual length. Restriction enzymes are positioned over their own recognition sites on the illustrations. The one arrow line into which many lines join together illustrates ligation. In the illustration for the DNA fragment obtained by the digestion of the pBluescript II SK-hGCSF vector with restriction enzymes Find III and Xba I, thicker lines stand for exons. In the other illustrations, exons and introns are indiscriminately expressed.

Figure 8:
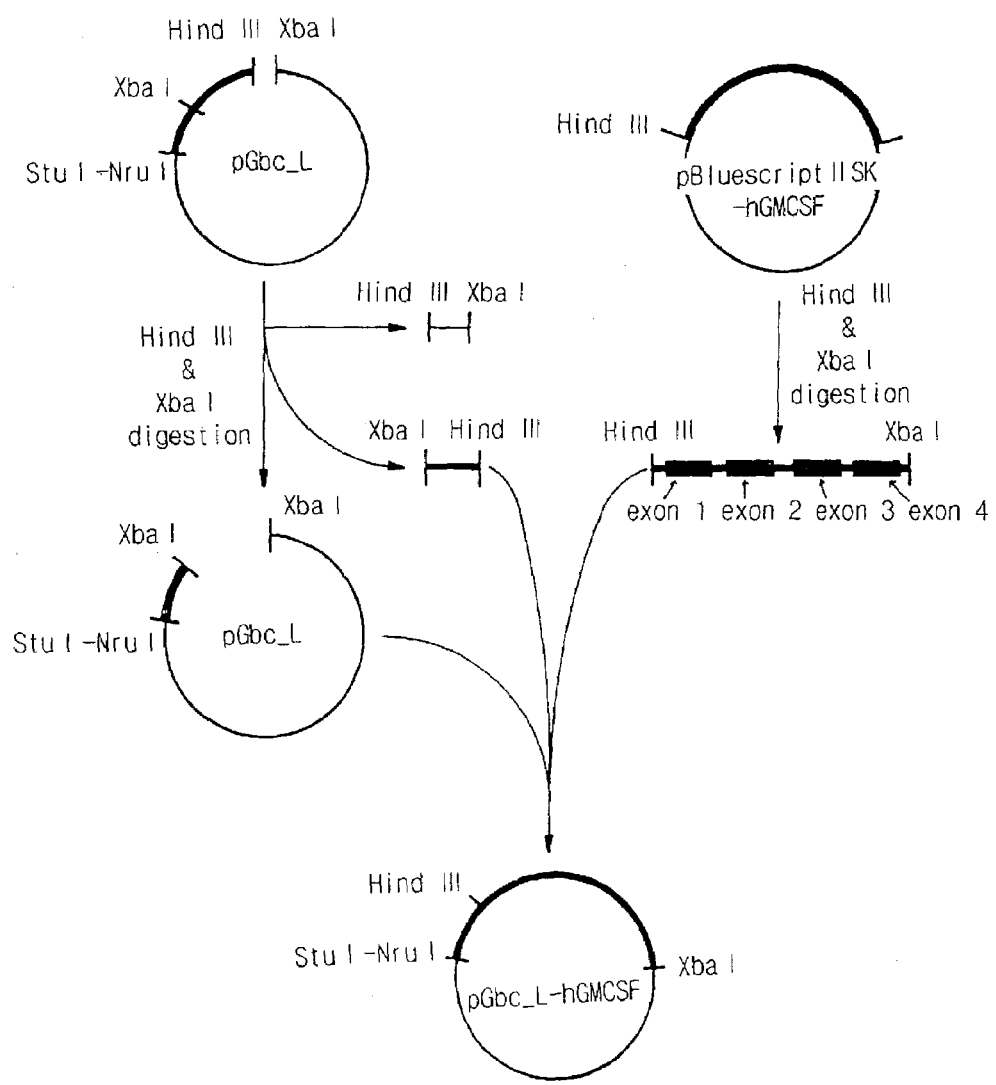
FIG. 8 is a schematic diagram illustrating the recombination of the vector pGbc_L with a hGMCSF gene, according to the present invention

FIG. 8 is a schematic diagram showing a procedure for the recombination between the plasmid pGbc_L and the hGMCSF gene.

In this figure, the length of each of the plasmids and DNA fragments does not reflect the scale of its actual length. Restriction enzymes are positioned over their own recognition sites on the illustrations. The one arrow line into which many lines join together illustrates ligation. In the illustration for the DNA fragment obtained by the digestion of the pBluescript II SK-hGMCSF vector with restriction enzymes Hind III and Xba I, thicker lines stand for exons. In the other illustrations, exons and introns are indiscriminately expressed.

Figure 9:
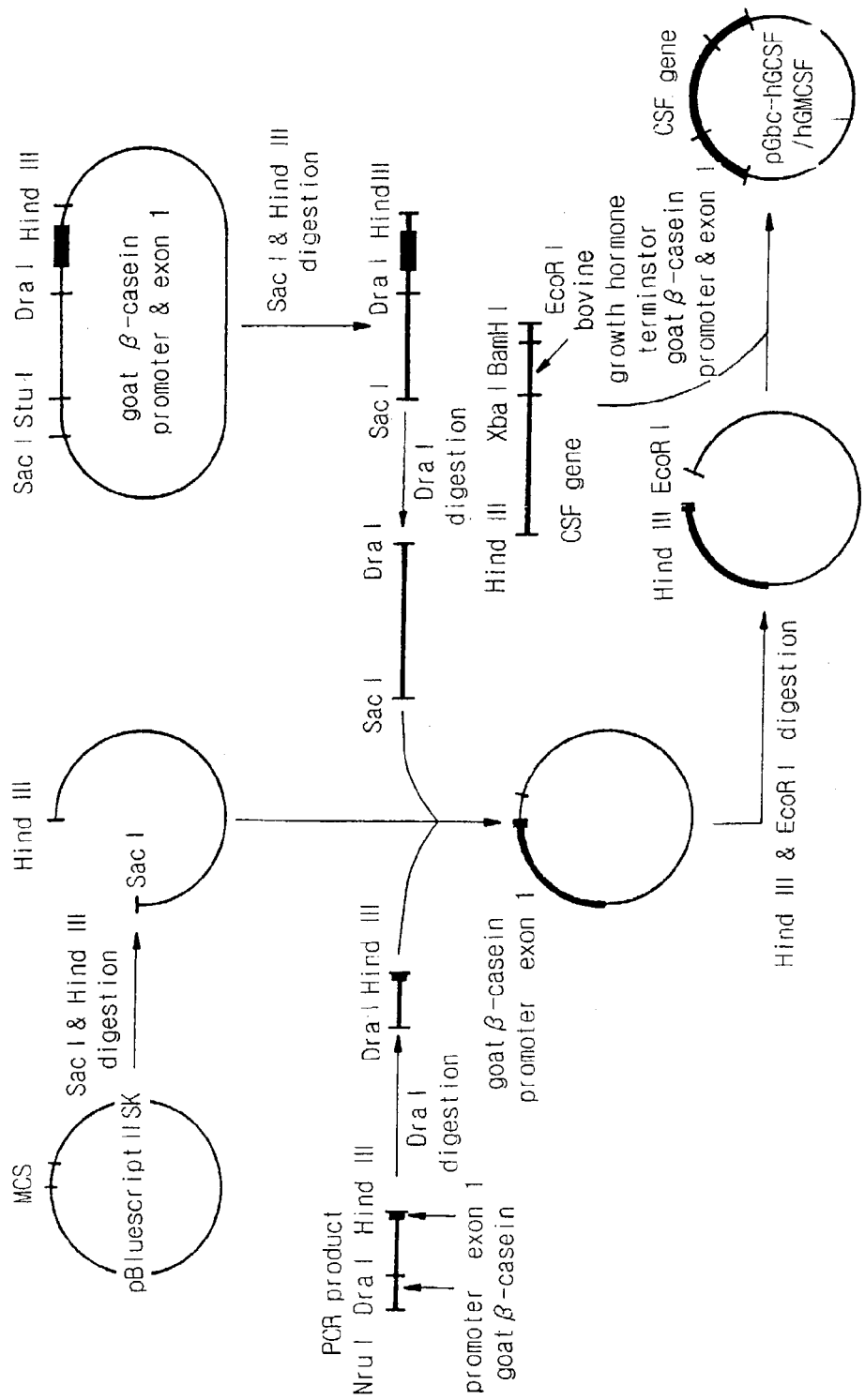
FIG. 9 is a schematic diagram illustrating the recombination of the vector pGbc with a hGCSF gene or a hGCSF gene, according to the present invention.

FIG. 9 shows a recombination of the pGbc vectors with hGCSF and hGMCSF genes.

In this figure, the length of each of the plasmids and DNA fragments does not reflect the scale of its actual length. Restriction enzymes are positioned over their own recognition sites on the illustrations. The one arrow line into which many lines join together illustrates ligation. In the illustrations for goat β-casein promoter & exon 1 and PCR product, thicker lines stand for exons.

Figure 10:
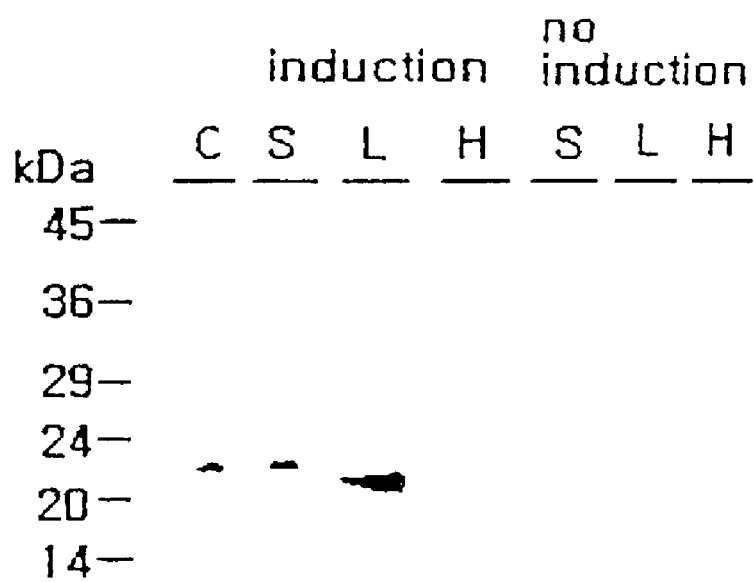
FIG. 10 shows a Western blotting analysis for the hGM-CSF proteins produced from the mouse mammary gland tissue-derived HC11 cells which are transfected with a recombinant vector pGbc_L or pGbc_S carrying a hGM-CSF gene, according to the present invention.

Referring to FIG. 10, there is shown a qualitative analysis for the expression of hGM-CSF in HC11 cells by a Western blotting technique. Proteins for this Western blotting are obtained from the HC11 cells, a cell line derived from the mouse mammary gland tissue, which are transfected with each of the mammalian expression vectors pGbc_S and pGbc_L, each containing an hGM-CSF gene, by inducing the cells into expression.

Figure 11:
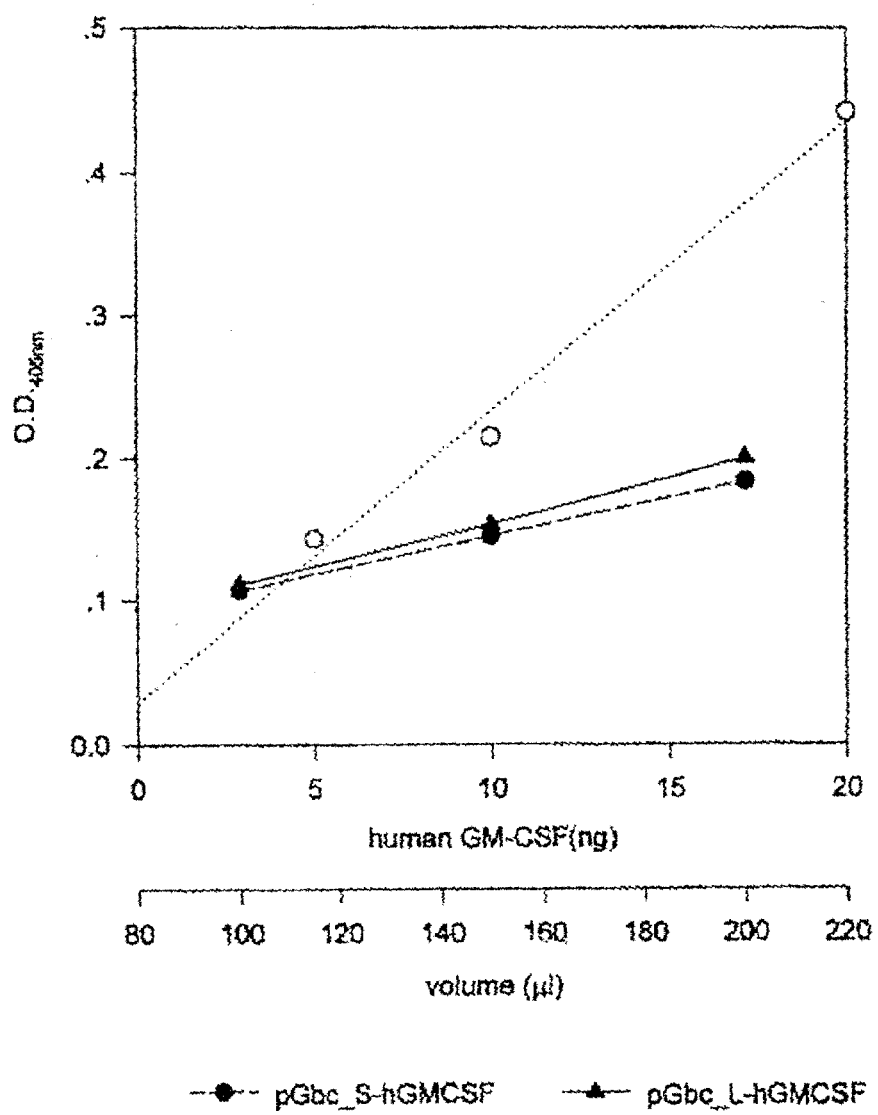
FIG. 11 is an ELISA graph for the hGM-CSF proteins produced from the mouse mammary gland tissue-derived HC11 cells which are transfected with a recombinant vector pGbc_L or pGbc_S carrying a hGM-CSF gene, according to the present invention.

Referring to FIG. 11, there is shown a quantitative analysis for the expression of hGM-CSF in HC11 cells by ELISA. Proteins for ELISA are obtained from the HC11 cells transfected with each of the mammalian expression vectors pGbc_S and pGbc_L, in which an hGM-CSF gene is cloned, by inducing the cells into expression.

Figure 12:
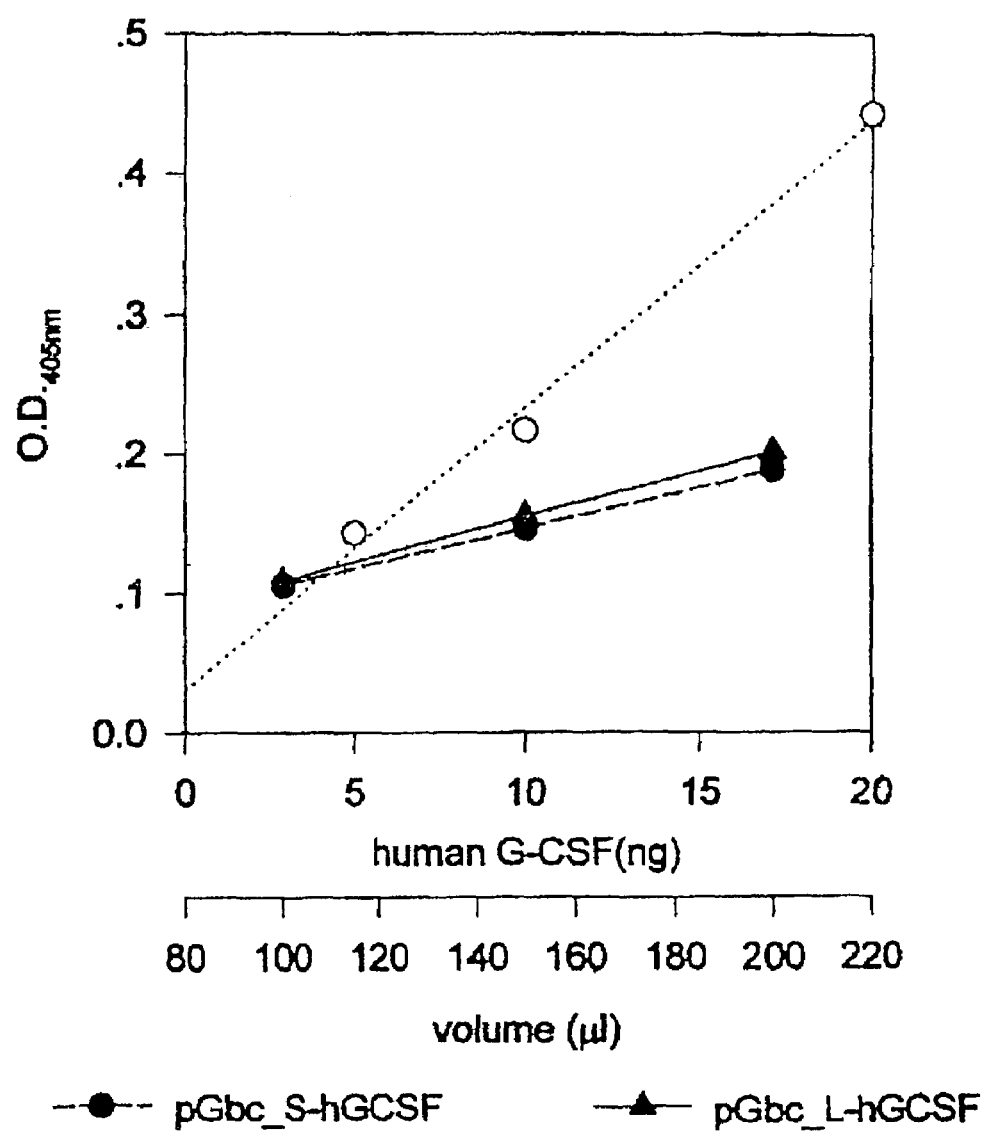
FIG. 12 is an ELISA graph for the hG-CSF protein produced from the mouse mammary gland tissue-derived HC11 cells which are transfected with a recombinant vector pGbc_L or pGbc_S carrying a hG-CSF gene, according to the present invention.

Referring to FIG. 12, there is shown a quantitative analysis for the expression of hG-CSF in HC11 cells by ELISA. Proteins for ELISA are obtained from the HC11 cells transfected with each of the mammalian expression vectors pGbc_S and pGbc_L, in which an hG-CSF gene is cloned, by inducing the cells into expression.

Figure 13:
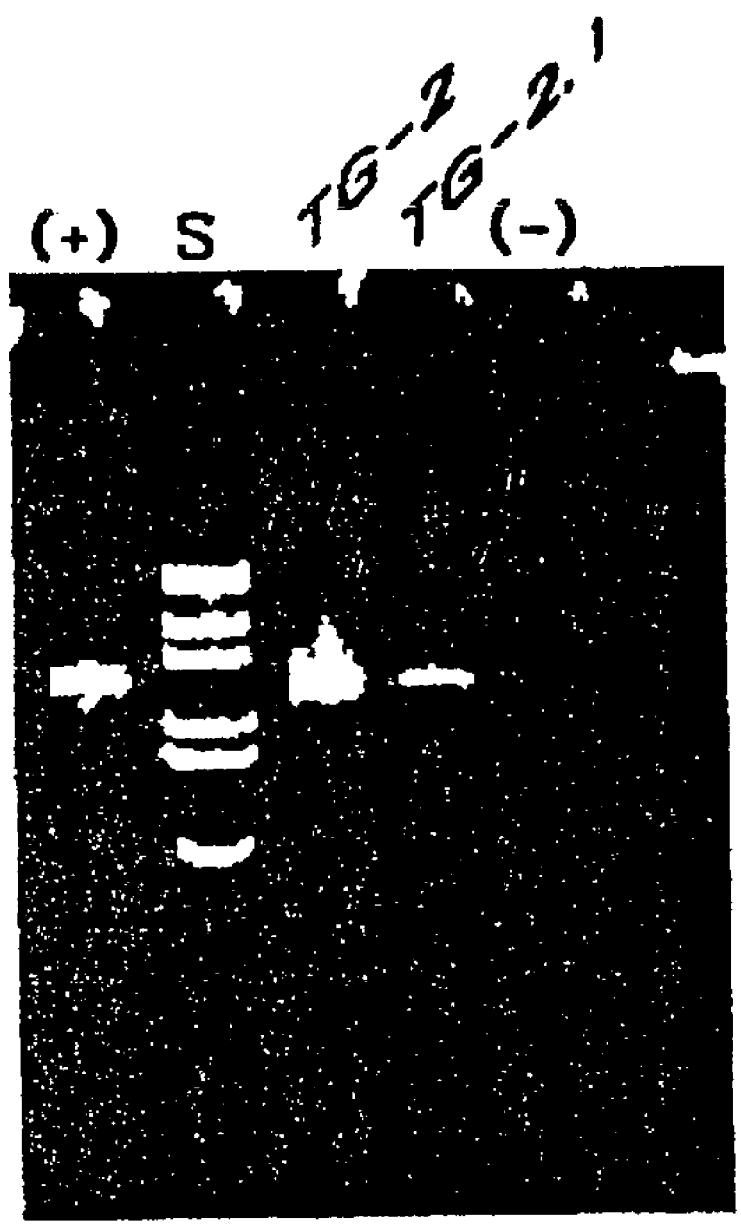
FIG. 13 is a photograph of the PCR products obtained by using the genomic DNAs of transgenic mice as templates.

FIG. 13 is a photograph showing the electrophoresis of PCR products of hGCSF genes on an agarose gel. In the figure, Lane (+) denotes an hGCSF PCR product using as a template the plasmid pGbc-hGSF. A PCR product, using as a template the genomic DNA of the transgenic mice which are born from a surrogate mouse in whose womb an oosperm transfected with the plasmid pGbc-hGCSF is nidated, is electrophoresed on Lane TG-2. TG-2.1 stands for the transgenic progenies from TG-2. On Lane (−) is run a PCR product which uses as a template the genomic DNA of non-transgenic, that is, normal mice.

Figure 14:
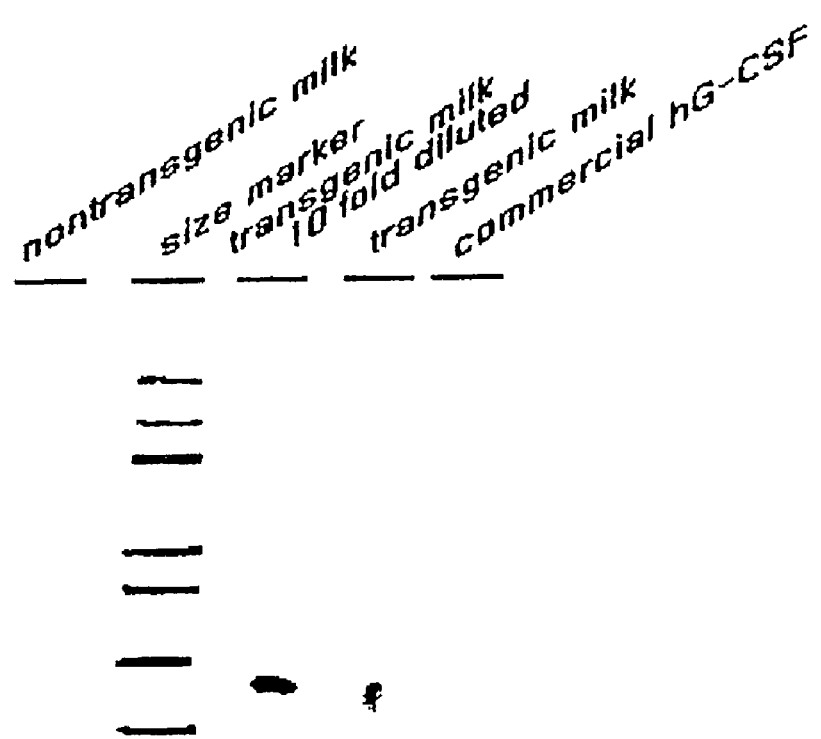
FIG. 14 shows a Western blotting analysis for the hG-CSF proteins secreted in the milk from the transgenic mice, according to the present invention.

Referring to FIG. 14, there is shown a qualitative analysis for the expression of hG-CSF in the milk secreted from transgenic mice by a Western blotting technique. Proteins for this Western blotting are obtained from the milk secreted from the transgenic mice into which the mammalian expression vectors pGbc_S and pGbc_L, each containing an hG-CSF gene, are introduced.

Figure 15:
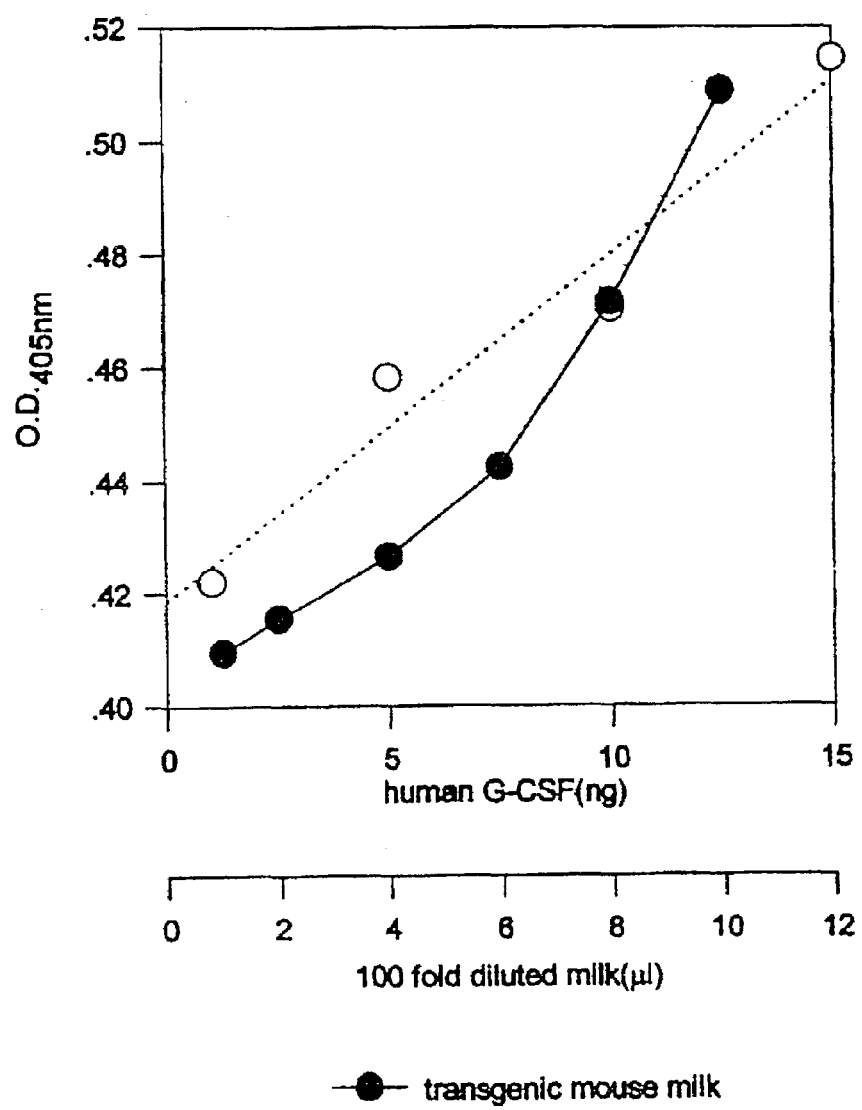
FIG. 15 is an ELISA graph for the hG-CSF proteins secreted in the milk from the transgenic mice, according to the present invention.

Referring to FIG. 15, there is shown a quantitative analysis for the expression of hG-CSF in the milk secreted from transgenic mice by ELISA. Proteins for ELISA are obtained from the milk secreted from the transgenic mice into which the mammalian expression vectors pGbc_S-hGCSF and pGbc_L-hGCSF are introduced.

Figure 16:
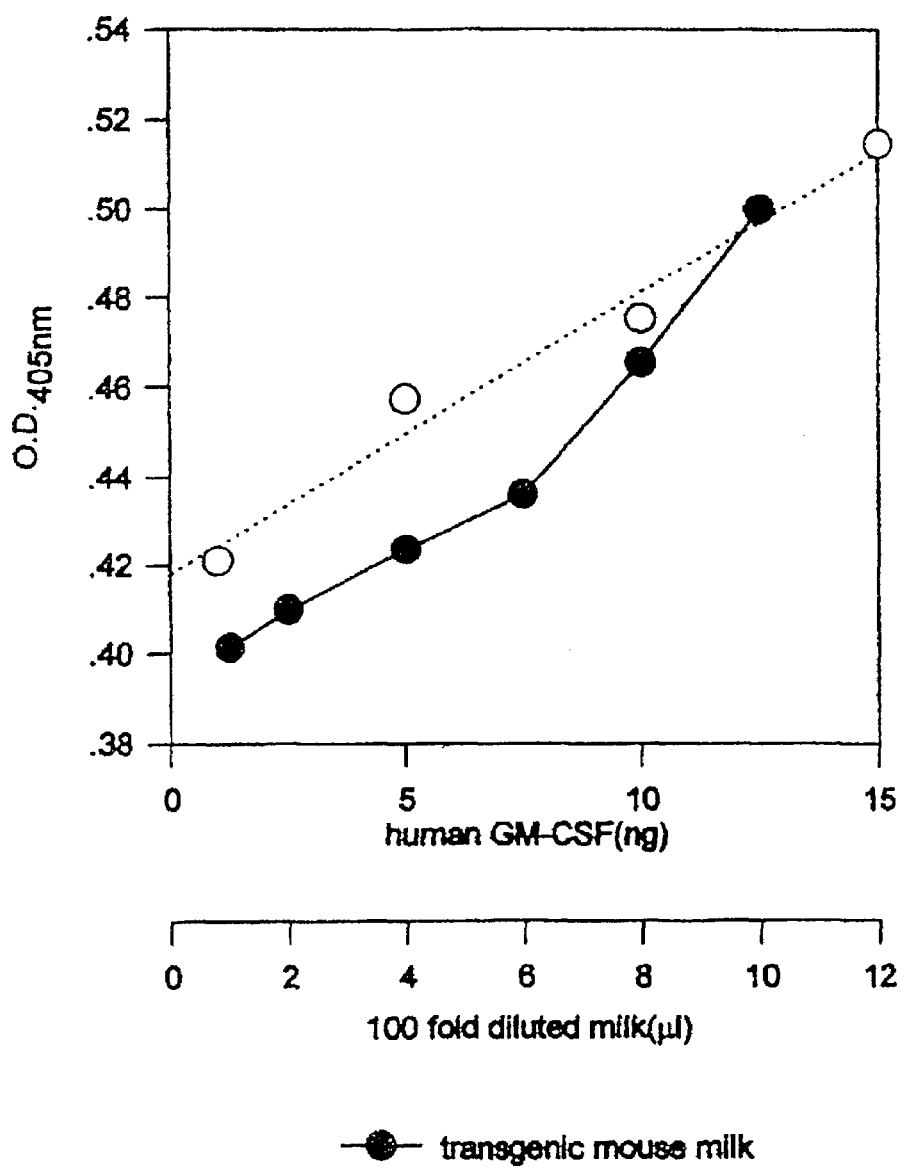
FIG. 16 is an ELISA graph for the hGM-CSF proteins secreted in the milk from the transgenic mice, according to the present invention.

Referring to FIG. 16, there is shown a quantitative analysis for the expression of hG-CSF in the milk secreted from transgenic mice by ELISA. Proteins for ELISA are obtained from the milk secreted from the transgenic mice into which the mammalian expression vectors pGbc_S-hGMCSF and pGbc_L-hGMCSF are introduced.

A better understanding of the present invention may be obtained in light of the following examples which are set forth to illustrate, but are not to be construed to limit the present invention.

EXAMPLE I

Construction of the Expression Vectors for HC11 Cell Using Goat β-casein Promoter site and Bovine Growth Hormone Terminator.

1) Construction of pGbc_S Vector

From a vector pBluescript II SK (Stratagene) in Which a DNA fragment including the promoter site, exon 1, intron 1 and exon 2 of a goat β casein gene was subcloned, a stretch of DNA which covered from 501 nucleotides to one nucleotide on the 5' side of the translation start codon for exon 1, was obtained by a PCR using primers CAS-F1 (SEQ ID NQ:6) and CAS-R1 (SEQ ID NO:7). Which had a base sequence of 5'-TGA TCG, CGA GTC CAC CAG GCT CTA CTG TC-3' and 5'-GAG AAG CTT AAT GGA TAA TGA TCT GA-3', respectively. The PCR consisted of 35 thermal cycles in which heating was performed in the order of at 94° C. for 3 min, at 55° C. for 1 min and at 72° C. for 1 min for the first cycle, in the order of at 94° C. for 1 min, at 55° C. for 1 min and at 72° C. 1 min for cycles 2–34, and in the order of at 94° C. for 1 min, at 55° C. for 1 min and at 72° C. for 5 min for the last cycle.

In a mammalian expression vector pRc/RSV which was digested with endonucleases Nru I and Hind III to open it and remove its LTR, the PCR product, after being also double-digested with the same endonucleases, was inserted by ligation. In result, a novel plasmid pGbc_S was obtained, as summarized in FIG. 3.

2) Construction of pGbc_L Vector

The truncated PCR product of the above 1) was treated with a restriction enzyme Dra I. The Dra I/Hind III-truncated DNA fragment thus obtained was isolated by electroelution. Separately, from the vector pBluescript II SK (Stratagene) in which a DNA fragment including the promoter site, exon 1, intron 1 and exon 2 of a goat β casein gene was subcloned, a Stu I/Dra I-truncated DNA fragment including the promoter and a partial exon 1 extending to one nucleotide on the upstream side of the translation start codon, was obtained by enzymatic cleavage and by isolation on agarose gel. The two DNA fragments were inserted together in a pRC/RSV vector which was opened by the double-digestion with restriction enzymes Nru I and Hind III, to make a novel plasmid pGbc_L. This procedure is summarized in FIG. 4.

3) Identification of pGbc_S and pGbc_L Constructs

The successful construction of plasmids pGbc_S and pGbc_L was confirmed by base sequencing analysis. The base sequencing analysis was performed by using a Sequenase kit Ver 2.0, provided by Amersham U.S.A., according to the protocol of the provider. For the sequencing, two primers V1 (SEQ ID NO:8) and V2 (SEQ ID NO:9) were designed to have a base sequence of 5'-AGG CAA GGC TTG ACC GAC-3' and 5'-GGA GGG GCA AAC AAC AGA TG-3', respectively.

EXAMPLE II

Recombination Between hGCSF Gene and Mammalian Expression Vector for HC11 Cell

An hGCSF gene was inserted in each of the vectors pGbc_S and pGbc_L according to the recombination strategy illustrated in FIGS. 5 and 7. In the recombination, the β-casein exon 1 was directly linked to the exon 1 of the hG-CSF gene while the translation start codon for the exon 1 of the hG-CSF gene was kept available.

In more detail, first, the pUC 19 vector in which an hG-CSF gene was subcloned, was digested with BamH I and Xba I and electrophoresed on an agarose gel to separate the resulting two DNA fragments from each other. These two DNA fragments, which consisted of Fragment I and the other fragment, were separately purified using a Geneclean II kit, commercially available from BIO101. Fragment 1 was believed to comprise exon 2 to poly A signal. The other fragment comprising the vector and exon 1 was cut with a restriction enzyme Pst I and then, the smaller fragments cut were run on an agarose gel to separate them from each other. Purification using a Geneclean II kit, commercially available from BIO101 afforded Fragment 2 which comprised one nucleotide on the 5' side of the translation start codon through one nucleotide on the 5' side of the exon 2. Fragment 1 and Fragment 2 together were inserted in a plasmid pBluescript II SK by ligation to give a novel recombinant plasmid pBluescript II SK-hGCSF. This plasmid was double-cut with restriction enzymes Hind III and Xba I to obtain a modified hG-CSF gene fragment which was, then, inserted in a pGbc_S vector which was previously opened by digestion with Hind III and Xba I. In result, a novel recombinant plasmid pGbc_S-hGCSF was obtained.

Separately, a pGbc_L vector was opened by enzymatic digestion with Hind III and Xba I. After being treated with an alkali phosphatase and electrophoresed on an agarose gel, the opened pGbc_L vector was purified using a Geneclean II kit. A DNA fragment obtained by the endonuclease digestion of a goat β-casein promoter and a modified hGCSF gene fragment obtained by double digestion of the pBluescript II SK-hGCSF with Hind III and Xba I are together ligated to the opened vector, to give a novel recombinant plasmid pGbc_L-hGCSF.

The successful construction of the novel recombinant plasmids pGbc_S-hGCSF and pGbc_L-hGCSF was confirmed by base sequencing analysis. The base sequencing analysis was performed by using a Sequenase kit Ver 2.0, provided by Amersham U.S.A., according to the protocol of the provider. For the sequencing, two primers V1 (SEQ ID NO:8), V2 (SEQ ID NO:9) and P1 (SEQ ID NO:10) were designed to have a base sequence of 5'-AGG CAA GGC TTG ACC GAC-3', 5'-GGA GGG GCA AAC AAC AGA TG-3', and 5'-CAC TAT TGG TTT TAT TTC-3', respectively.

EXAMPLE III

Recombination between hGMCSF Gene and Mammalian Expression Vectors pGbc_S and pGbc_L for HC11 Cells The recombination was carried out by following the strategy illustrated in FIGS. 6 and 8.

First, the hGMCSF gene which was subcloned in a pUC19 vector, was extracted by digestion with restriction enzymes BamH I and EcoR I and by purification with a Geneclean II kit (BIO101) from an agarose gel on which the digested DNA fragments were electrophoresed. Then, the hGMCSF gene was inserted by ligation to a pBluescript II SK vector (Stratagene) which had been digested with the same endonucleases and then, with a bovine alkali phosphatase, to afford a recombinant plasmid pBluescript II SK-hGMCSF. A modified gene was recovered from this recombinant plasmid by digestion with Hind III and Xba I, electrophoresis on an agarose gel and purification with a Geneclean II kit (BIO101) and then, ligated to a pGbc_S vector which were previously treated with the same endonuclease and then with a bovine alkali phosphatase, to construct a novel plasmid pGbc_S-hGMCSF.

Similarly, a novel plasmid pGbc_L-hGMCSF was constructed by ligating a DNA fragment obtained by the endonuclease digestion of a goat β-casein promoter and a modified hGMCSF gene fragment obtained by the double digestion of the pBluescript II SK-hGMCSF with Hind III and Xba I to an opened pGbc_L vector which was obtained by the treatment with restriction enzymes Hind III and Xba I and then with a bovine alkali phosphatase and by the purification from an agarose gel on which electrophoresis was done.

The successful construction of the expression vectors is confirmed through base sequencing analysis using the primers VI, V2 and P1.

EXAMPLE IV

Construction of the Vector for Transfection

Mammalian expression vectors for tranfection with the same gene structure as that of FIG. 1, were constructed according to the recombination strategy of FIG. 9. They could be prepared by inserting a goat β-casein promoter site, a physiological activating substance gene and a bovine growth hormone terminator in a pBluescript II SK vector (Stratagene).

In more detail, from a goat β-casein gene or its fragment, a DNA fragment including the promoter site and a partial exon 1 extending to one nucleotide on the upstream side of the translation start codon, was obtained by cutting with Sac I and Hind III. After a purification procedure comprising the steps of extracting with a phenol:chloroform 1:1 solution, precipitating with 95% ethanol, and dissolving in distilled water, the DNA fragment was further cut with a restriction enzyme Dra I. Electrophoresis on an agarose gel and purification by use of a Geneclean II kit (BIO101) afforded Fragment 1, which comprised the partial exon 1.

Separately, a stretch of DNA which covered from 501 nucleotides to one nucleotide on the 5' side of the translation start codon for the exon 1 of the β-casein gene, was obtained by a PCR using the primers CAS-F1 and CAS-R1 and, then, cleaved by Dra I and Hind III. Fragment 2, which comprised the exon 1, was obtained by electroelution.

Fragments 1 and 2 were inserted by ligation in a pBluescript II SK vector (Stratagene) which had been enzymatically treated with Sac I and Hind III and then, with a bovine alkali phosphatase. The recombinant plasmid thus obtained was opened by double-digestion with Hind III and EcoR I. To this opened cloning site, a DNA fragment in which a physiological activating substance gene was linked to a bovine growth hormone terminator, was inserted.

The success of the above recombination procedure was confirmed through a base sequencing analysis using the primer P1.

EXAMPLE V

Expression of hGMCSF in Mouse Mammary Gland-Derived HC11 Cells

The plasmids pGbc_S-hGMCSF and pGbc_L-hGMCSF which resulted from the recombination between the plasmid pGbc_S and the hGMCSF gene and between the plasmid pGbc_L and the hGMCSF gene, respectively, in Example III, were purified using QIAGEN-tip 100 (Qiagen) before being introduced into HC11 cells.

After being transformed with each of the plasmids, E. coli cells were inoculated in 150 ml of LB medium containing ampicillin at a concentration of 100 μg/ml and incubated at 37° C. for 10 hours with agitation. The cells were harvested by centrifugation, and the plasmids were purified from the cells using the protocol recommended by Qiagen.

Transfection of the purified plasmids into HC11 cells was accomplished by using an electroporator, commercially available from Invitrogen. HC11 cells were densely grown on T75 flasks for tissue culture in a 5% $CO_2$, 37° C. incubator until they covered 80% of the bottom area of the flask. Thereafter, they were floated with a trypsin solution (Gibco BRL) and suspended with a PBS buffer. This cell suspension was centrifuged at 1,500 rpm to harvest the cells which was, then, washed with a chilled PBS buffer. A small volume of the cell solution was taken to count cell number and the remaining volume was precipitated by centrifugation at 1,500 rpm. The precipitated mass of the cells was diluted with a PBS buffer to give a cell suspension having $3 \times 10^6$ – $1 \times 10^7$ cells/500 μl.

20 μg of the purified plasmid and 500 μl of the cell suspension were added in a 0.4 cm cuvette which was, then, put in ice for 10 min. After being set to any one of any one of 71, 250, 500 and 1000 μF, the electroporator was controlled in voltage and resistances. The electroporator was charged for 3 min in order to apply pulses to the cuvette which was brought into the chamber of the electroporator. Then, the cuvette was put in ice for 10 min, after which the cell suspension in the cuvette was added with 1 ml of a growth medium and poured on 4 ml of a growth medium in a T25 flask. After culturing for 24–48 hours in a 5% $Co_2$, 37° C. incubator, the cells were provided a fresh medium RPMI 1640 (Gibco BRL), supplemented with fetal bovine serum at a final concentration of 10%, epidermal growth factor at 10 ng/ml, insulin at 5 μg/ml, and antibiotics gentamicin at 50 μg/ml and geneticin (Sigma) at 200 μg/ml, to select the transfected cells. The selective medium was refreshed every second or third day. At 7 days after culturing in the selective medium, only the cells into which the plasmids were introduced, survived. These transfected cells continued to grow densely.

After the selection, the selective medium was changed with an induction medium comprising RPMI 1640 media (Gibco BRL) supplemented with insulin at a final concentration of 5 μg/ml, geneticin (Sigma) at 200 μg/ml, gentamicin 50 μg/ml, goat prolacitin at 5 μg/ml and dexamethasone at 1 μM. The cells were cultured in a 5% $Co_2$, 37° C. incubator for 4 days without refreshing the medium.

The hGMCSF produced as a result of the expression induction of the gene, was secreted into the medium. A Western blotting technique was used for the qualitative analysis of the secreted product while an enzyme linked immunosorbent assay (ELISA) was for a quantitative analysis. As a primary antibody for the Western blotting, an anti-human GM-CSF mouse Ig G was used for the analysis of the expression of human granulocyte macrophage colony stimulating factor. A horse radish peroxidase-conjugated anti-mouse Ig G was used as a secondary antibody for the Western blotting. For ELISA, anti-human GM-CSF goat Ig G polyclonal antibodies were first attached on 96 well plates which were, then, treated with the expressed product as a corresponding antigen or with a commercially available factor used as a standard. To these were linked the anti-human GM-CSF monoclonal antibodies which were the same as used in the Western blotting. The resulting antibody complexes were treated with alkali phosphatase-conjugated anti-mouse Ig G monoclonal antibody with the aim of inducing a coloring reaction (Ed Harlow and Davis Lane (1989) *Antibodies A Laboratory Manual*, Cold Spring harbor Laboratory Press, New York).

The data obtained from the Western blot and ELISA are given in FIGS. 10 and 11 and show that the novel recombinant vectors pGbc_S and pGbc_L both induce the protein to be expressed at a level of 40 ng/ml.

EXAMPLE VI

Expression of hGCSF in HC11 Cells

The plasmids pGbc_S-hGCSF and pGbc_L-hGCSF which resulted from the recombination between the plasmid pGbc_S and the hGCSF gene and between the plasmid pGbc_L and the hGCSF gene, respectively, were purified using QIAGEN-tip 100 (Qiagen) in the same manner as that of Example V before being introduced into HC11 cells. The introduction was achieved by a calcium phosphate coprecipitation method or an electroporation method. Following transfection, culture in a selective medium comprising the same composition as that of Example V left geneticin-resistant colonies only. These screened colonies were transferred onto T75 flasks and grown densely thereon. The cells were provided with a fresh induction medium containing lactating hormones, prolactin and dexamethasone, and cultured for 4 days, after which the medium and the cells were separated by centrifugation. The supernatant was utilized for Western blotting analysis and ELISA. The data obtained are given in FIG. 12, showing that the novel recombinant vectors pGbc_S and pGbc_L both induce the protein to be expressed at a level of 40 ng/ml.

EXAMPLE VII

Expression of hGMCSF in Transgenic Mice

The novel recombinant vector pGbc-hGCSF which resulted from the recombination between the vector pGbc and the hGMCSF gene, was purified with the aid of QIAGEN tip 100 and digested with restriction enzymes BssH I and Kpn I, followed by extraction with a Geneclean II kit (BIO101) from an agarose gel. For use in microinjection, the extracted vectors were further purified by following the protocol recommended by Schleicher & Schuell and then, dialyzed in a solution comprising 10 mM Tris•Cl (pH 7.2) and 10 mM EDTA, to give a DNA solution at a concentration of 40 ng/ml.

Into the male pronuclear site of a CBA line mouse oosperm, the finally purified expression vector was introduced by microinjection. This oosperm was nidated in the womb of a surrogate mother. From the tails of the progenies of the surrogate mother, genomic DNAs were isolated. Which mouse was transgenic was identified by PCR, as shown in FIG. 13, and confirmed with a Southern blotting analysis.

The progeny mice which were confirmed to have the gene introduced into their genomic DNAs were let to coupulate non-transgenic, normal mice to produce next generation progenies. 10 days after birth, the transgenic parturient mice were segregated from the their offspring for 3 hours. Following peritoneal injection of oxytocin along with an anesthetic, milk was extracted from the parturient mice.

The expression level of the genes was assayed in the same manner as in cell level, using Western blotting and ELISA for qualitative and quantitative analyses, respectively. The antibodies used in these analyses were the same as those suggested in Example V. The results are given in FIGS. 14 and 15. From the Western blot, it is apparent that a protein from the transgenic mice is the same as a commercially available hGCSF (Gibco BRL) and is expressed through the mammary gland tissue of the transgenic mice, as shown in FIG. 14. The data of the ELISA show that the hGCSF is expressed at a level of 150 ng/μl, as shown in FIG. 15.

EXAMPLE VIII

Expression of hGMCSF in Transgenic Mice

The novel recombinant vector pGbc-hGMCSF which resulted from the recombination between the vector pGbc and the hGMCSF gene, was purified with the aid of QIAGEN tip 100 and digested with restriction enzymes BssH I and Kpn I, followed by extraction with a Geneclean II kit (BIO101) from an agarose gel. For use in microinjection, the extracted vectors were further purified by following the protocol recommended by Schleicher & Schuell and then, dialyzed in a solution comprising 10 mM Tris•Cl (pH 7.2) and 10 mM EDTA, to give a DNA solution at a concentration of 40 ng/ml.

Into the male pronuclear site of a CBA line mouse oosperm, the finally purified expression vector was introduced by microinjection. This oosperm was nidated in the womb of a surrogate mother. From the tails of the progenies of the surrogate mother, genomic DNAs were isolated. Which mouse was transgenic was identified by PCR, followed by confirmation with a Southern blotting analysis.

Milk was taken from the trangenic mice and subjected to Western blotting and ELISA. The data of the Western blotting analysis in which a commercial hGMCSF (BIO101) was used as a positive control, shows that a protein from the transgenic mice is hGCSF and is expressed through its mammary gland tissue. From the ELISA, the hGCSF from the transgenic mice was revealed to be expressed at a level of 130 ng/μl, as shown in FIG. 16.

INDUSTRIAL APPLICABILITY

As described hereinbefore, the mammary gland tissue-specific expression systems using the β-casein promoter site of Korean native goats, in accordance with the present invention, enable physiological activating substances to be produced in vivo, that is, in mammary gland tissue-derived cells as well as in transgenic animals. Therefore, the proteins obtained are those which experience the posttranslational modification and thus can maintain their normal activity in the human body. Also, the expression systems according to the present invention make it possible to easily produce the proteins at a great amount. Where the proteins are produced in a cell level, a lactating hormone is used as a potent expression inducer. In the case of transgenic animals, the proteins can be easily obtained through the milk secreted therefrom. Thus, the is scale-up of the production of the proteins to the extent of industrialization can be achieved. Additionally, the mammary gland tissue-specific expression systems according to the present invention are very advantageous in isolating and purifying the desired protein with ease and safety.

The following are the great industrial advantages which the mammary gland tissue-specific expression system of the present invention will bring about.

First, because the target proteins which are produced in the mammary gland tissue-specific expression systems which employ the β-casein promoter site of Korean native goats, experience the same posttranslational modification as that which the corresponding naturally occurring proteins do, the target proteins can sustain their activity in the human body. Overcoming the limitation the conventional expression systems using *E. coli* as a host has, the expression systems of the present invention can be equally applied to all kinds of the physiological activating substances.

Second, the goat β-casein promoter used in the present invention enable the accompanied structural gene to be inducibly expressed at a great amount, leading to a great decrease in the production cost of corresponding proteins. It is well known that the expression of the goat β casein gene can be induced in a highly level by the hormones from the mammary gland tissue, that is, lactating hormones. The mammary gland tissue-derived cells transfected with the expression systems employing the goat β-casein promoter can produce the desired proteins at an amount of 40 ng/ml by the treatment with a trace amount of an inducer, a lactating hormone, while the transgenic animals with the expression systems can produce the desired proteins at an amount of 130–150 ng/μl by the animals' own hormones. To our knowledge, greater amounts of these products are possible to obtain by modifying the length of the goat β-casein promoter site and expression conditions. Therefore, the present invention suggests a novel mass-production method for proteins.

Thirdly, the scale-up for the mass-production of target proteins can be easily achieved through the mammary gland tissue-specific expression systems of the present invention without requiring a significant cost. Because the target proteins are secreted in milk, the scale-up can be achieved simply by increasing the number of the transgenic animals. This can save the cost further required to scale up protein production from a laboratory level to an industrial level. That is, the production cost of the physiological activating substances can be significantly reduced by use of the mammary gland tissue-specific expression systems of the present invention.

Fourth, the present invention is based on the simpleness and harmlessness of the proteins secreted from the mammary gland. There are a few kinds of proteins which are expressed in mammary gland tissues, so that the proteins each can be isolated by ordinary techniques. Further, no harmful proteins are detected from milk.

The present invention has been described in an illustrative manner, and it is to be understood the terminology used is intended to be in the nature of description rather than of limitation. Many modifications and variations of the present invention are possible in light of the above teachings. For example, other various physiological activating substances can be expressed through the expression systems of the invention with a little aid of well-known DNA recombination techniques. Therefore, the present invention should not be confined only to the expression of hG-CSF or hGM-CSF, which is illustrated through the specification. It is to be understood that within the scope of the appended claims, the invention may be practiced otherwise than as specifically described.

What is claimed is:

1. A method for producing human Granulocyte Colony Stimulating Factor (hGCSF) or human Granulocyte Macrophage Colony Stimulating Factor (hGMCSF), comprising:
   a) providing any one of the recombinant vectors selected from the group consisting of pGbc_L deposited under accession number KCTC 0514BP, pGbc_S deposited under accession number KCTC 0513BP, and pGbc deposited under accession number KCTC 0515BP;
   b) inserting a polynucleotide encoding hGCSF or hGMCSF, and a termination-regulating region into said vector;
   c) introducing said vector produced in step (b) into a mouse;
   d) inducing the expression of the hGCSF or hGMCSF in conditions sufficient to induce expression and produce the hGCSF or hGMCSF.

2. The method of claim 1, wherein step c) is accomplished by microinjecting the vector produced in step b) into a male pronucleus of said mouse.

* * * * *

SEQUENCE LISTING

<160> NUMBER OF SEQ ID NOS: 10

<210> SEQ ID NO 1
<211> LENGTH: 2009
<212> TYPE: DNA
<213> ORGANISM: Artificial Sequence
<220> FEATURE:
<223> OTHER INFORMATION: Beta casein promoter sequence

<400> SEQUENCE: 1

```
aagcttcttt ctttagtata ttgttaagga tttcttgatc aagattttac ctacttttct      60
ggtccaattg gtgagagaca gtcataagga aatgctgtgt ttattgcaca atatgtaaag     120
catcttcctg agaaaataaa agggaaatgt tgaatgggaa ggatatgctt tcttttgtat     180
tccttttctg agaaatcaga cttttcacc tgtggccttg gcacaaaagc taacaaataa      240
aggcatatga agtagccaag gccttttcta gtatatctat gacactgagt tcatttcatc     300
atttattttc ctgacttcct cctgggtcca tatgagcagt cttagaatga atattagctg     360
aataatccaa atacatagta gatgttgatt tgggttttct aagcaatcca agacttgtat     420
gacagtaaga tgtattacca tccaacaaca cacatctcag catgatataa atgcaaggta     480
tattgtgaag aaaaattttt aattatgtca aagtgcttac tttagaaggt catctatctg     540
tcccaaagct gtgaatatat atattgaagg taatgaatag atgaagctaa ccttgtaaaa     600
atgagtagtg tgaatacaac tacaattatg aacatctgtc actaaagagg caaagaaact     660
tgaagattgc ttttgcaaat gggctcctat taataaaaag tacttttgag gtctggctca     720
gactctattg tagtacttag ggtaataccc tcctcctgta tgggctttca ttttctttct     780
tgcttccctc atttgccctt ccatgaatga ctagctgata aagcattgac tataaaagat     840
atgaggccaa acttgagctg tcccatttta ataaatctgt ataataatat tgttctacaa     900
aagtattatc taaataaatg ttactttctg tcttaaaatc cctcaacaaa tccccactat     960
ctagaggatc cgattgacat tccctggaat cacagcatgc tttgtctgcc attatctgac    1020
ccctttctct ttctctcttc tcacctccat ctactccttt ttccttgcaa ttcatgaccc    1080
agattcactg tttgatttgg cttgcatgtg tgtgtgctga gttgcgtctg actgttatca    1140
accccatgaa tgatagtcca ccaggctcta ctgtccatga aattttccag tcaagaatac    1200
tggagtggat tgcatttcct actccatttg attaatttag tgacttttaa atttctttt     1260 ccatattcgg gagcctattc ttccttttta gtctatactc tcttcactct tcaggtctaa    1320
ggtatcatcg tgtgcttgtt agcttgttac tttctccatt atagcttaag cactaacaac    1380
tattcaggtt ggcatgaaat tgtgttcttt gtgtggcctg tatatttctg ttgtgtatta    1440
```

```
gaatttaccc caagatctca aagacccact gaatactaaa gagacctcat tgtggttaca   1500
ataatttggg gactgggcca aaacttccgt gcatcccagc caagatctgt agctactgga   1560
caatttcatt tcctttatca gattgtgagt tattcctgtt aaaatgctcc ccagaatttc   1620
tggggacaga aaataggaa gaattcattt cctaatcatg cagatttcta ggaattcaaa    1680
tccactgttg gttttatttc aaaccacaaa attagcatgc cattaaatac tatatataaa   1740
cagccactaa atcagatcat tatccattca gcttctcctt cacttcttct cctctacttt   1800
ggaaaaaagg taagaatctc agatataatt tcagtgtatc tgctactcat ctttattttg   1860
gactaggtta aaatgtagaa agaacataat tgcttaaaat agatcttaaa aataagggtg   1920
tttaagataa ggtttacact attttcagca gatatgttaa aaaatagaag tgactataaa    1980
gacttgataa aaattatagg tgactgcaa                                     2009

<210> SEQ ID NO 2
<211> LENGTH: 28
<212> TYPE: DNA
<213> ORGANISM: Artificial Sequence
<220> FEATURE:
<223> OTHER INFORMATION: Cloning oligonucleotide

<400> SEQUENCE: 2
gctgagctct ttagtatatt gttaagga                                      28

<210> SEQ ID NO 3
<211> LENGTH: 26
<212> TYPE: DNA
<213> ORGANISM: Artificial Sequence
<220> FEATURE:
<223> OTHER INFORMATION: Cloning oligonucleotide

<400> SEQUENCE: 3
tgtcaagctt atcttaaaca ccctta                                        26

<210> SEQ ID NO 4
<211> LENGTH: 27
<212> TYPE: DNA
<213> ORGANISM: Artificial Sequence
<220> FEATURE:
<223> OTHER INFORMATION: Cloning oligonucleotide

<400> SEQUENCE: 4
gcataagctt tacactattt tcagcag                                       27

<210> SEQ ID NO 5
<211> LENGTH: 23
<212> TYPE: DNA
<213> ORGANISM: Artificial Sequence
<220> FEATURE:
<223> OTHER INFORMATION: Cloning oligonucleotide

<400> SEQUENCE: 5
atagtcgacc cagagttgtg gtc                                           23

<210> SEQ ID NO 6
<211> LENGTH: 29
<212> TYPE: DNA
<213> ORGANISM: Artificial Sequence
<220> FEATURE:
<223> OTHER INFORMATION: Primer oligonucleotide

<400> SEQUENCE: 6
tgatcgcgag tccaccaggc tctactgtc                                     29
```

```
<210> SEQ ID NO 7
<211> LENGTH: 26
<212> TYPE: DNA
<213> ORGANISM: Artificial Sequence
<220> FEATURE:
<223> OTHER INFORMATION: Primer oligonucleotide

<400> SEQUENCE: 7
gagaagctta atggataatg atctga                                          26

<210> SEQ ID NO 8
<211> LENGTH: 18
<212> TYPE: DNA
<213> ORGANISM: Artificial Sequence
<220> FEATURE:
<223> OTHER INFORMATION: Primer oligonucleotide

<400> SEQUENCE: 8
aggcaaggct tgaccgac                                                   18

<210> SEQ ID NO 9
<211> LENGTH: 20
<212> TYPE: DNA
<213> ORGANISM: Artificial Sequence
<220> FEATURE:
<223> OTHER INFORMATION: Primer oligonucleotide

<400> SEQUENCE: 9 ggagggcaa acaacagatg                                                  20

<210> SEQ ID NO 10
<211> LENGTH: 18
<212> TYPE: DNA
<213> ORGANISM: Artificial Sequence
<220> FEATURE:
<223> OTHER INFORMATION: Primer oligonucleotide

<400> SEQUENCE: 10
cactattggt tttatttc                                                   18
```